(12) United States Patent
Kalla et al.

(10) Patent No.: US 7,449,473 B2
(45) Date of Patent: Nov. 11, 2008

(54) SUBSTITUTED PYRROLO[3,2-D]PYRIMIDIN-2,4-DIONES AS $A_{2B}$ ADENOSINE RECEPTOR ANTAGONISTS

(75) Inventors: Rao Kalla, Cupertino, CA (US); Elfatih Elzein, Fremont, CA (US); Tim Marquart, Santa Clara, CA (US); Thao Perry, San Jose, CA (US); Xiaofen Li, Mountain View, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 423 days.

(21) Appl. No.: 10/973,167

(22) Filed: Oct. 26, 2004

(65) Prior Publication Data

US 2005/0119287 A1 Jun. 2, 2005

Related U.S. Application Data

(60) Provisional application No. 60/516,019, filed on Oct. 31, 2003.

(51) Int. Cl.
*C07D 471/04* (2006.01)
*A61K 31/519* (2006.01)
*A61P 11/06* (2006.01)

(52) U.S. Cl. .................... 514/265.1; 544/280
(58) Field of Classification Search ............ 544/280; 514/265.1
See application file for complete search history.

(56) References Cited

U.S. PATENT DOCUMENTS

| 5,593,975 | A | 1/1997 | Cristalli |
| 5,714,494 | A | 2/1998 | Connell et al. |
| 6,117,878 | A | 9/2000 | Linden |
| 6,825,349 | B2 | 11/2004 | Kalla et al. |
| 2005/0020532 | A1 | 1/2005 | Elzein et al. |
| 2005/0070558 | A1 | 3/2005 | Videl Juan et al. |

FOREIGN PATENT DOCUMENTS

| EP | 0764647 A1 | 3/1997 |
| WO | WO 01/94350 A1 | 12/2001 |

OTHER PUBLICATIONS

Stefanachi et. al. (Tetrahedron Letters, 2003, 44(10), 2121-2123).*

Stefanachi, A et al., "Fast and Highly Efficient One-Pot Synthesis of 9-Deazaxanthines"; *Tetrahedron Letters*; Elsevier Science Publishers, Amsterdam, NL, vol. 44, No. 10; Mar. 3, 2003, pp. 2121-2123, XP004410067.

Carotti, A. et al, "8-Substituted-9-Deazaxanthines as Adenosine Receptor Ligands: Design, Synthesis and Structure-affinity Relationships at A2B"; *European Journal of Medicinal Chemistry*, Editions Scientifique Elsevier, Paris, FR, vol. 39, No. 10, Oct. 2004, pp. 879-887, XP004584651.

Grahner, B., et al., "Synthesis and Structure-activity Relationships of Deazaxanthines: Analogs for Potent A1-and A2-Adenosine Receptor Antagonists"; *Journal of Medicinal Chemistry*, American Chemical Society, Washington, U.S.; vol. 37, No. 10, 1994, pp. 1526-1534, XP001093706.

Hayallah, A., et al., "1,8-Disubstituted Xanthine Derivatives" Synthesis of Potent $A_{2B}$-Selective Adenosine Receptor Antagonists; *Journal of Medicinal Chemistry*, American Chemical Society; vol. 45, No. 7; 2002; pp. 1500-1510.

\* cited by examiner

*Primary Examiner*—Brenda L. Coleman
*Assistant Examiner*—Susanna Moore
(74) *Attorney, Agent, or Firm*—J. Elin Hartrum

(57) ABSTRACT

Disclosed are novel compounds that are $A_{2B}$ adenosine receptor antagonists having the following structure:

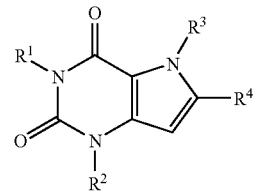

wherein $R^1$ and $R^2$ are independently chosen from hydrogen, optionally substituted alkyl, optionally substituted cycloalkyl, optionally substituted aryl, and optionally substituted heteroaryl, and $R^4$ is an optionally substituted heteroaryl moiety. The compounds of the invention are useful for treating various disease states, including asthma, chronic obstructive pulmonary disorder, pulmonary inflammation, emphysema, diabetic disorders, inflammatory gastrointestinal tract disorders, immunological/inflammatory disorders, cardiovascular diseases, neurological disorders, and diseases related to angiogenesis.

16 Claims, No Drawings

SUBSTITUTED PYRROLO[3,2-D]PYRIMIDIN-2,4-DIONES AS $A_{2B}$ ADENOSINE RECEPTOR ANTAGONISTS

CROSS REFERENCE TO RELATED APPLICATIONS

This application claims priority to U.S. Provisional Patent Application Ser. No. 60/516,019, filed Oct. 31, 2003.

FIELD OF THE INVENTION

The present invention relates to $A_{2B}$ adenosine receptor antagonists, and to their use in treating mammals for various disease states, such as pulmonary disorders, inflammatory disorders, gastrointestinal disorders, immunological/inflammatory disorders, neurological disorders, and cardiovascular diseases due to both cellular hyperproliferation and apoptosis, and the like. The invention also relates to methods for the preparation of such compounds, and to pharmaceutical compositions containing them.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, inflammation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148-153), and $A_3$ adenosine receptors modulate cell proliferation processes.

Adenosine $A_{2B}$ receptors are ubiquitous, and regulate multiple biological activities. For example, adenosine binds to $A_{2B}$ receptors on endothelial cells, thereby stimulating angiogenesis. Adenosine also regulates the growth of smooth muscle cell populations in blood vessels. Adenosine stimulates $A_{2B}$ receptors on mast cells, thus modulating Type I hypersensitivity reactions. Adenosine also stimulates gastrosecretory activity by ligation with $A_{2B}$ in the intestine.

While many of these biological effects of adenosine are necessary to maintain normal tissue homeostasis, under certain physiological changes it is desirable to modulate its effects. For example, the binding of $A_{2B}$ receptors stimulates angiogenesis by promoting the growth of endothelial cells. Such activity is necessary in healing wounds, but the hyperproliferation of endothelial cells promotes diabetic retinopathy. Also, an undesirable increase in blood vessels occurs in neoplasia. Accordingly, inhibition of the binding of adenosine to $A_{2B}$ receptors in the endothelium will alleviate or prevent hypervasculation, thus preventing retinopathy and inhibiting tumor formation.

$A_{2B}$ receptors are found in the colon in the basolateral domains of intestinal epithelial cells, and when acted upon by the appropriate ligand act to increase chloride secretion, thus causing diarrhea, which is a common and potentially fatal complication of infectious diseases such as cholera and typhus. $A_{2B}$ antagonists can therefore be used to block intestinal chloride secretion, and are thus useful in the treatment of inflammatory gastrointestinal tract disorders, including diarrhea.

Insensitivity to insulin exacerbates diabetes and obesity. Insulin sensitivity is decreased by the interaction of adenosine with $A_{2B}$ receptors. Thus, blocking the adenosine $A_{2B}$ receptors of individuals with diabetes or obesity would benefit patients with these disorders. It has also been demonstrated that $A_{2B}$-antagonists cause a reduction of blood glucose levels, and thus would be particularly useful in the treatment of type-II diabetes.

Another adverse biological effect of adenosine acting at the $A_{2B}$ receptor is the over-stimulation of cerebral IL-6, a cytokine associated with dementias and Alzheimer's disease. Inhibiting the binding of adenosine to $A_{2B}$ receptors would therefore mitigate those neurological disorders that are produced by IL-6.

Type I hypersensitivity disorders, such as asthma, hay fever, and atopic eczema, are stimulated by binding to $A_{2B}$-receptors of mast cells. Therefore, blocking these adenosine receptors would provide a therapeutic benefit against such disorders.

There are several compounds presently used in the treatment of asthma. For example, theophylline is an effective antiasthmatic agent, even though it is a poor adenosine receptor antagonist. However, considerable plasma levels are needed for it to be effective. Additionally, theophylline has substantial side effects, most of which are due to its CNS action, which provide no beneficial effects in asthma, and to the fact that it non-specifically blocks all adenosine receptor subtypes.

Additionally adenosine treatment, such as inhaled adenosine (or adenosine monophosphate), provokes bronchoconstriction in asthmatics, but not in the normal population. This process is known to involve mast cell activation, in that it releases mast cell mediators, including histamine, PGD2-β-hexosaminidase and tryptase, and because it can be blocked by specific histamine $H_1$ blockers and chromolyn sodium. Accordingly, there is an intrinsic difference in the way adenosine interacts with mast cells from asthmatics, and thus $A_{2B}$ antagonists are particularly useful in modulating mast cell function or in the activation of human lung cells.

Accordingly, it is desired to provide compounds that are potent $A_{2B}$ antagonists (i.e., compounds that inhibit the $A_{2B}$ adenosine receptor), fully or partially selective for the $A_{2B}$ receptor, useful in the treatment of various disease states related to modulation of the $A_{2B}$ receptor, for example cancer, rheumatoid arthritis, asthma, chronic obstructive pulmonary disorder, pulmonary fibrosis, and retinopathy.

SUMMARY OF THE INVENTION

It is an object of this invention to provide $A_{2B}$ receptor antagonists. Accordingly, in a first aspect, the invention relates to compounds of Formula I:

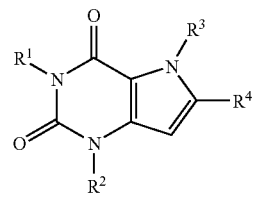

Formula I wherein:

$R^1$ and $R^2$ are independently chosen from hydrogen, optionally substituted alkyl, optionally substituted cycloalkyl, optionally substituted aryl, and optionally substituted heteroaryl;

$R^3$ is chosen from hydrogen, hydroxy, optionally substituted alkyl, optionally substituted cycloalkyl, optionally substituted aryl, and optionally substituted heteroaryl; and $R^4$ is an optionally substituted heteroaryl moiety, with the proviso that $R^4$ cannot be an unsubstituted five-membered monocyclic heteroaryl ring containing a single S or O hetero atom.

A second aspect of this invention relates to a method of using the compounds of Formula I in the treatment of a disease or condition in a mammal that is amenable to treatment with an $A_{2B}$ receptor antagonist (i.e., inhibiting an adenosine receptor characterized as $A_{2B}$), comprising administering to a mammal in need thereof a therapeutically effective dose of a compound of Formula I. Such diseases include, but are not limited to, asthma, chronic obstructive pulmonary disorder, pulmonary fibrosis, emphysema, diabetic disorders, including, but not limited to, type II diabetes, inflammatory gastrointestinal tract disorders, including diarrhea, inflammatory pulmonary disorders, cardiovascular diseases such as atherosclerosis, immunological/inflammatory disorders such as rheumatoid arthritis, neurological disorders such as senile dementia, Alzheimer's disease, and Parkinson's disease, and diseases related to angiogenesis, for example diabetic retinopathy and cancer.

A third aspect of this invention relates to pharmaceutical formulations, comprising a therapeutically effective amount of a compound of Formula I and at least one pharmaceutically acceptable excipient.

One preferred group of compounds of Formula I are those in which $R^1$ and $R^2$ are independently hydrogen or optionally substituted lower alkyl, $R^3$ is hydrogen or hydroxide, and $R^4$ is an optionally substituted five or six membered monocyclic heteroaryl moiety.

Within this group, a first preferred class of compounds include those in which $R^1$ and $R^2$ are independently lower alkyl optionally substituted by cycloalkyl, preferably n-propyl, ethyl, or methyl, and $R^4$ is an optionally substituted five membered heteroaryl moiety.

A preferred subclass of compounds within this class includes those compounds in which $R^4$ contains at least two heteroatoms selected from the group consisting of nitrogen, oxygen, and sulfur. A further preferred group within this subclass contains those compounds wherein $R^4$ contains 2 nitrogen heteroatoms, such as an imidazole or pyrrazole moiety.

Another preferred subclass of compounds are those compounds in which $R^4$ contains a single O or S heteroatom and is substituted with 1 to 3 substituents independently selected from the group consisting of optionally substituted alkyl, optionally substituted heteroaryl, and optionally substituted aryl moieties. In yet another preferred subclass of compounds, $R^4$ contains a single N heteroatom and is optionally substituted with 1 to 3 substituents independently selected from the group consisting of optionally substituted alkyl, optionally substituted cycloalkyl, optionally substituted heteroaryl, and optionally substituted aryl moieties.

A second preferred class of compounds include those in which $R^1$ and $R^2$ are independently lower alkyl optionally substituted by cycloalkyl, preferably n-propyl, ethyl, or methyl, and $R^4$ is an optionally substituted six membered heteroaryl moiety. Within this class, a preferred subclass of compounds are those in which $R^4$ is a pyridine moiety optionally substituted with 1 to 3 substituents independently selected from the group consisting of optionally substituted alkyl, optionally substituted heteroaryl, optionally substituted cycloalkyl, and optionally substituted aryl moieties.

It will, of course, be understood that the above-described substituent combinations are only exemplary and that any and all other subcombinations of substituent groups are within the scope of the invention and are expressly encompassed herein.

At present, the preferred compounds are:

8-(1-methyl-1H-pyrrol-2-yl)-1,3-dipropyl-1H-pyrrolo[3,2-d]pyrimidine-2,6-dione;

8-(1-(3-(trifluoromethyl)benzyl)-1H-pyrazol-4-yl)-1,3-dipropyl-1H-pyrrolo[3,2-d]pyrimidine-2,6-dione;

8-(1-(3-(trifluoromethyl)benzyl)-1H-pyrazol-4-yl)-1-ethyl-3-propyl-1H-pyrrolo[3,2-d]pyrimidine-2,6-dione;

8-(1-benzyl-1H-pyrazol-4-yl)-1,3-dipropyl-1H-pyrrolo[3,2-d]pyrimidine-2,6-dione;

8-(1-benzyl-1H-pyrazol-4-yl)-7-hydroxy-1,3-dipropyl-1H-pyrrolo[3,2-d]pyrimidine-2,6-dione;

8-(1-(3-fluorobenzyl)-1H-pyrazol-4-yl)-1,3-dipropyl-1H-pyrrolo[3,2-d]pyrimidine-2,6-dione;

8-(pyridin-4-yl)-7-hydroxy-1,3-dipropyl-1H-pyrrolo[3,2-d]pyrimidine-2,6-dione;

8-(pyridin-2-yl)-7-hydroxy-1,3-dipropyl-1H-pyrrolo[3,2-d]pyrimidine-2,6-dione;

8-(5-(thiophen-2-yl)isoxazol-3-yl)-1,3-dipropyl-1H-pyrrolo[3,2-d]pyrimidine-2,6-dione;

8-(1-(3-(trifluoromethyl)benzyl)-1H-pyrazol-4-yl)-7-hydroxy-1,3-dipropyl-1H-pyrrolo[3,2-d]pyrimidine-2,6-dione;

8-(N-oxypyridin-4-yl)-1,3-dipropyl-1H-pyrrolo[3,2-d]pyrimidine-2,6-dione;

6-(1-(3-(trifluoromethyl)benzyl)-1H-pyrazol-4-yl)-1-methyl-3-propyl-1H-pyrrolo[3,2-d]pyrimidine-2,4(3H,5H)-dione;

6-(1-(3-(trifluoromethyl)benzyl)-1H-pyrazol-4-yl)-1-cyclopropylmethyl-3-propyl-1H-pyrrolo[3,2-d]pyrimidine-2,4(3H,5H)-dione; and 6-(1-(3-(trifluoromethyl)benzyl)-1H-pyrazol-4-yl)-1-isobutyl-3-propyl-1H-pyrrolo[3,2-d]pyrimidine-2,4(3H,5H)-dione.

DEFINITIONS AND GENERAL PARAMETERS

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene(—CH(Cl)—), aminoethylene (—CH(NH$_2$)CH$_2$—), methylaminoethylene(—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane(—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl) propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH$_2$), 1-propylene or allyl (—CH$_2$CH═CH$_2$), isopropylene, (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

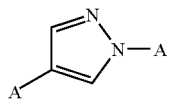

where A represents the point of attachment.

Unless otherwise constrained by the definition for the heteroaryl or heteroarylene substituent, such heteroaryl or heteroarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, aryl, substituted aryl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) in which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is n-propyl, $R^2$ is n-propyl, $R^3$ is hydrogen, and $R^4$ is 1-(3-(trifluoromethyl)benzyl)-1H-pyrazol-4-yl,

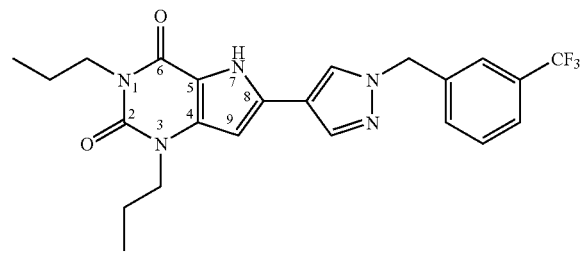

which is named:
8-(1-(3-(trifluoromethyl)benzyl)-1H-pyrazol-4-yl)-1,3-dipropyl-1H-pyrrolo[3,2-d]pyrimidine-2,6-dione.

Synthetic Reaction Parameters

The terms "solvent," "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I where $R^3$ is hydrogen may be prepared as shown in Scheme I.

SCHEME 1

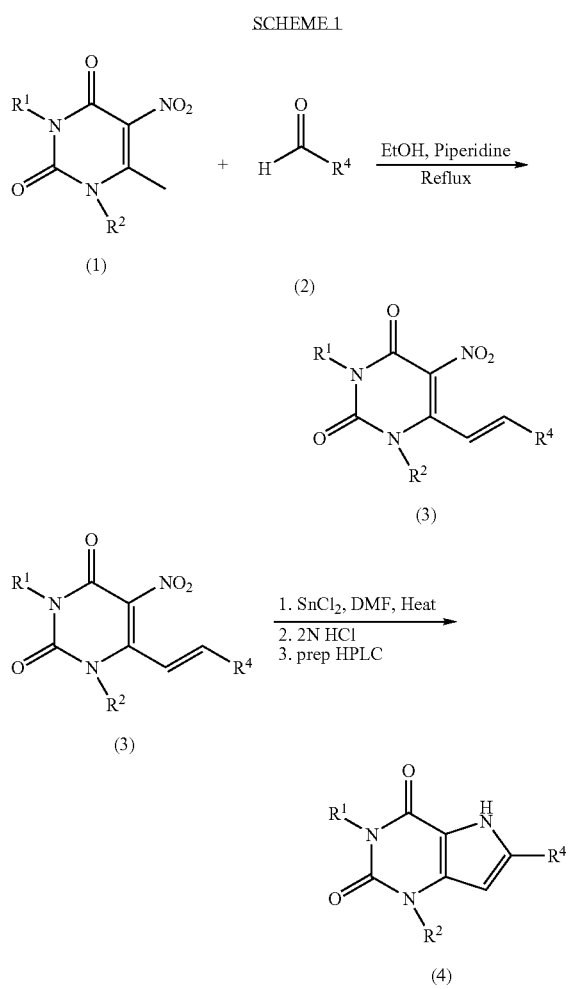

As shown in Scheme 1, a suitable nitro-uracil precursor, (1), is mixed with an appropriate aldehyde, (2), and piperidine, in a suitable solvent such as ethanol. The solution is heated to reflux for approximately 10-20 hours. After reflux, the mixture is concentrated and purified using conventional methods, such as thin layer chromatography, to produce the vinyl-nitro-uracil (3).

Once the $R^4$ containing vinyl group has been added to the uracil framework, the resulting compound (3) is placed in a polar solvent such as N,N'-dimethyl formamide (DMF). A catalytic amount of $SnCl_2$ is added to the solution and the mixture is heated to approximately 150° C. for 1 to 2 hours. After cooling, an acid solution, such as 2N HCl, is added, thereby causing the final product (4) to precipitate. Removal and purification of the final product (4) may be accomplished using conventional techniques that will be readily apparent to one of ordinary skill in the art.

Preparation of the Nitro-Uracil Precursor

The nitro-uracil precursor may be prepared as shown in Scheme 2 below.

SCHEME 2

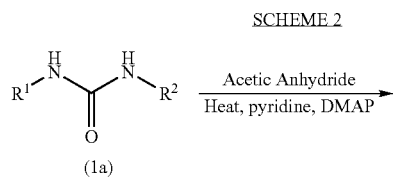

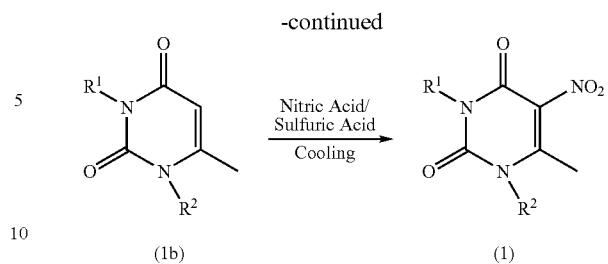

As shown in Scheme 2, a disubstituted urea derivative (1a) is reacted with acetic anhydride in a solution of pyridine and 4-(dimethylamino)pyridine (DMAP). The mixture is subjected to mild heating, i.e., approximately 100° C. for 1 to 2 hours, thereby producing the uracil compound (1b). The reaction mixture is then cooled and the solvent removed under vacuum. The residue may then be dissolved in an appropriate solvent, i.e., dichloromethane, and washed, concentrated, and purified using conventional methods.

Small portions of the uracil compound (1b) are then added to a cooled solution of concentrated sulfuric acid and nitric acid. The reaction is stirred at zero degrees for approximately 2 hours. The reaction mixture is then poured over ice, resulting in the formation of a green amorphous solid, which is removed by filtration and washed copiously with water. Finally, the resulting nitro-uracil precursor (1) is dissolved in an appropriate solvent, i.e., dichloromethane, and then washed, concentrated, and purified using conventional methods.

The aforementioned method is suitable for preparing nitro-uracil precursors wherein $R^1$ and $R^2$ are identical. A method for preparing nitro-uracil precursors having differing $R^1$ and $R^2$ moieties is presented in Scheme 3 below.

SCHEME 3

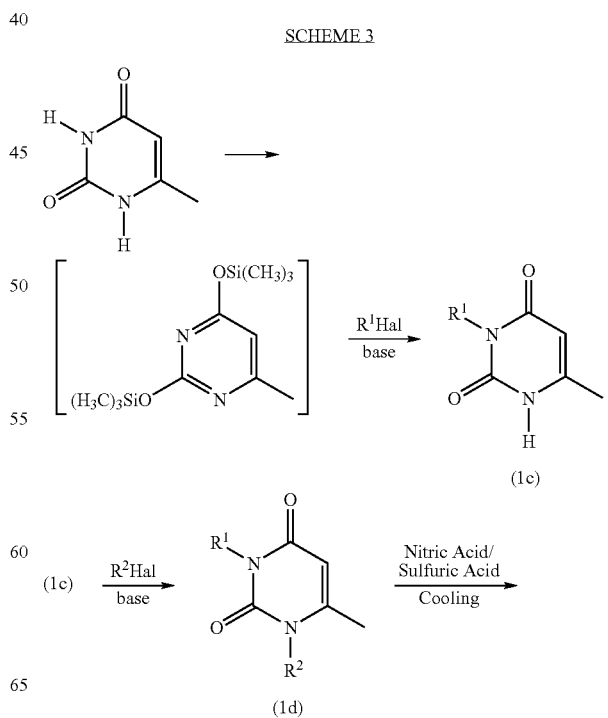

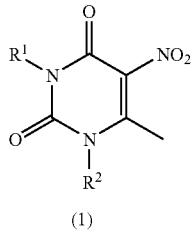

(1)

The commercially available compound 6-methyluracil is first silylated, for example by reaction with hexamethyldisilazane in the presence of a catalyst, for example ammonium sulfate. The reaction is carried out at about reflux temperature, for about 1-10 hours. When the reaction is substantially complete, the silylated compound thus produced is isolated conventionally and reacted at about reflux, for about 12 to 16 hours with a compound of formula $R^1Hal$, where $R^1$ is as defined above other than hydrogen. Preferably, this reaction is carried out in the absence of a solvent. When the reaction is substantially complete, the product of formula (1c) is isolated by conventional means.

If modification on the second nitrogen atom in the ring is also desired, the compound of formula (1c) may be further reacted with a compound of formula $R^2Hal$, where $R^2$ is as defined above other than hydrogen. The resulting, disubstituted compound (1d) may then be isolated by conventional means.

The compound of formula (1c) or (1d) is then dissolved in a cooled solution of concentrated sulfuric acid and nitric acid. The reaction is stirred at zero degrees for approximately 2 hours. When the reaction is substantially complete, the resulting nitro-uracil precursor (1) is isolated by conventional means as discussed above with respect to Scheme 2.

Alternatively, disubstituted uracil derivates may be prepared according to the method presented in Scheme 4.

SCHEME 4

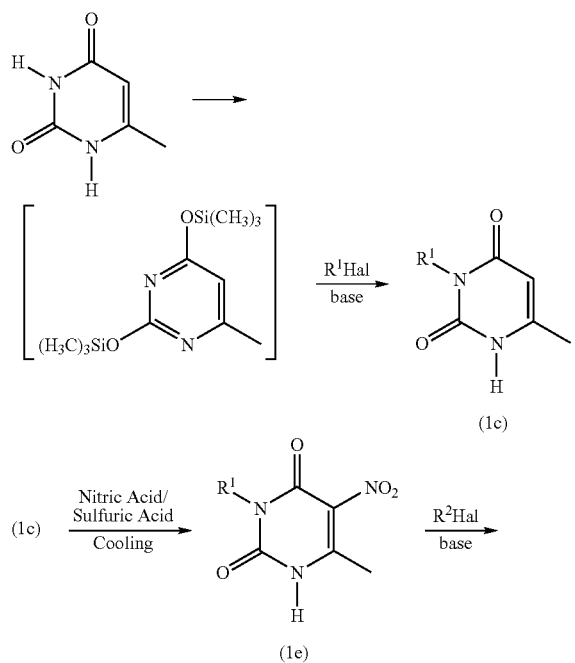

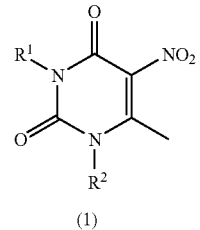

(1)

In this method, a commercially available compound 6-methyluracil is first silylated and then reacted with a compound of formula $R^1Hal$, as described in with respect to Scheme 3. In Scheme 4 however, the nitro group is added to the (1c) compound prior to addition of the $R^2$ substituent.

Preparation of the Aldehyde Precursor

The aldehyde precursor may be any commercially available aldehyde having the structure of formula (2) wherein $R^4$ is as defined above. Preferred $R^4$ groups have the structure XY, where X is a heteroarylene group and Y is an optionally substituted aryl or alkaryl group. Aldehyde precursors containing these types of $R^4$ moieties may be prepared as shown in Scheme 5 below.

SCHEME 5

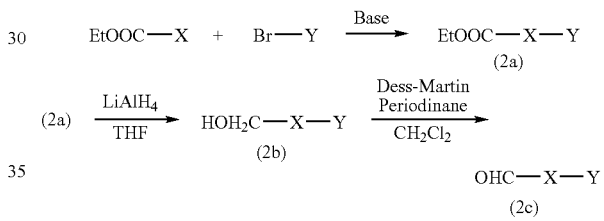

As shown in Scheme 5, a halide derivative of the desired Y moiety is reacted with an ethyl ester of the desired X moiety in the presence of base. The solution is heated to approximately 60° C. and stirred for 10-20 hours. After cooling and filtration to remove any undesired solids, the filtrate is concentrated and purified using conventional techniques.

In order to convert the resulting ethyl ester to the analogous alcohol, the product (2a) is dissolved in an appropriate solvent, such as THF, and cooled to 0° C. under inert atmosphere. A catalytic amount of lithium aluminum hydride is then added dropwise and the solution is allowed to warm to room temperature and is stirred for 1-2 hours. Saturated ammonium chloride solution is then added slowly until gas evolution ceases. All solvent is then removed in vacuo. The resulting alcohol, compound (2b), is then purified using conventional techniques.

The aldehyde is then formed using a solution of Dess-Martin Periodinane, 1,1,1-Triacetoxy-1,1-dihydro-1,2-benziodoxol-3(1H)-one, in dichloromethane. The solution is cooled and compound (2b) in dichloromethane is added dropwise. The reaction is allowed to stir at room temperature for approximately one hour and then concentrated. Diethyl ether may be used to precipitate out the resulting aldehyde, compound (2c), which is then removed by filtration and further purified using conventional techniques.

Preparation of Compounds Wherein $R^3$ is other than Hydrogen

Once a compound having the structure of formula (4) is prepared, it may be further modified to provided the desired $R^3$ substitution. This type of modification may be carried out using a conventional substitution reaction wherein a halide derivative of the desired $R^3$ substituent is reacted with the formula (4) compound in the presence of base. Methods of conducting such a reaction are well known and will be obvious to one of ordinary skill in the art.

It will also be obvious to one of ordinary skill in the art that compounds wherein $R^3$ is a hydroxy moiety will also be produced during the conversion of the formula (3) compound into the final formula (4) product.

Utility, Testing and Administration

General Utility

The compounds of Formula I are effective in the treatment of conditions that respond to administration of $A_{2B}$ adenosine receptor antagonists. Such conditions include, but are not limited to, at least one of rheumatoid arthritis, diarrhea, atherosclerosis, restenosis, diabetes, in particular type-II diabetes, macular degeneration, diabetic retinopathy, cancer, senile dementia, Alzheimer's disease, Parkinson's disease, traumatic brain injury, emphysema, chronic obstructive pulmonary disorder, pulmonary fibrosis, wound healing, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper, or other container. When the excipient serves as a diluent, in can be a solid, semi-solid, or liquid material (as above), which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (1b) Wherein $R^1$ and $R^2$ are Identical

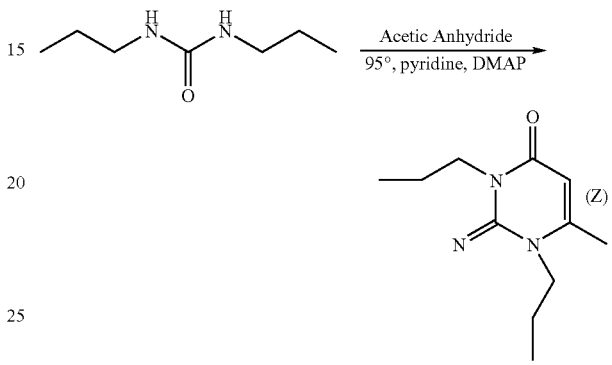

To a solution of N,N' Dipropyl urea (10.0 g, 69.4 mmol) in pyridine (60 ml) was added acetic anhydride (21.6 ml, 229 mmol) and 4-(dimethylamino)pyridine (8.5 g, 69.4 mmol). The mixture was heated to 95° C. for 1.5 hours. The reaction mixture was cooled and the solvent was removed under vacuum. The residue was then dissolved in dichloromethane (200 ml) and washed with 2N HCl (2×60 ml) and saturated sodium bicarbonate (2×60 ml). The organic layer was concetrated and purified using column chromatography (2:1 Hexane:Ethyl Acetate) to yield 6-methyl-1,3-dipropyl-1,3-dihydropyrimidine-2,4-dione(4.0 g, M+1=210.92)

EXAMPLE 2

Preparation of Compounds of Formula (1b), Wherein $R^1$ and $R^2$ are Identical

Using the procedure set out in Example 1, but replacing the dipropyl urea with other disubstituted ureas, the following compounds of formula (1b) are prepared:
1,3,6-triimethyl-1,3-dihydropyrimidine-2,4-dione;
6-methyl-1,3-diethyl-1,3-dihydropyrimidine-2,4-dione;
6-methyl-1,3-di(methoxyethyl)-1,3-dihydropyrimidine-2,4-dione;
6-methyl-1,3-di-n-butyl-1,3-dihydropyrimidine-2,4-dione;
6-methyl-1,3-diisobutyl-1,3-dihydropyrimidine-2,4-dione;
6-methyl-1,3-di(phenylethyl)-1,3-dihydropyrimidine-2,4-dione;
6-methyl-1,3-dicyclobutyl-1,3-dihydropyrimidine-2,4-dione;
6-methyl-1,3-di(pyrid-4-ylmethyl)-1,3-dihydropyrimidine-2,4-dione;
6-methyl-1,3-di(furan-3-ylmethyl)-1,3-dihydropyrimidine-2,4-dione;
6-methyl-1,3-di(4-methoxybenzyl)-1,3-dihydropyrimidine-2,4-dione;
6-methyl-1,3-di(4-trifluoromethylbenzyl)-1,3-dihydropyrimidine-2,4-dione; and 6-methyl-1,3-di(fluorobenzyl)-1,3-dihydropyrimidine-2,4-dione.

EXAMPLE 3

Preparation of a Compound of Formula (1c), 6-Methyl-3-propyl-1,3-dihydropyrimidine-2,4-dione

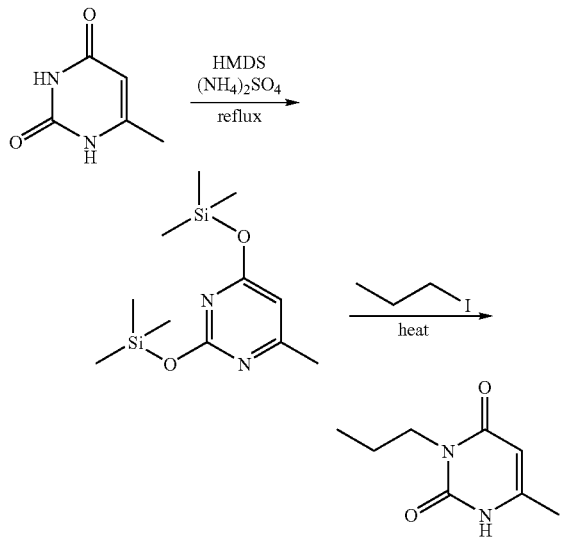

A suspension of 2,4-dihydroxy-6-methyluracil (20 g, 0.16 mol) and ammonium sulfate (1 g, 0.007 mol, 0.05 eq.) was stirred in HMDS (200 ml) at 130° C. for 16 h, during which time the reaction mixture becomes homogeneous. Excess HMDS was distilled off, and the reaction mixture was cooled to 100° C. To the above residual solution, iodopropane (62 ml, 0.64 mol) was added and the mixture was stirred at 100° C. for 48 h. The reaction mixture was cooled and poured into water. The product was extracted with dichloromethane (3×100 mL). The organic layer was washed with water, brine, and dried over $Na_2SO_4$. Removal of solvent gave the product as a solid material, which was washed with ether to get a clean 6-methyl-3-propyl-1,3-dihydropyrimidine-2,4-dione (12 g) and used as such for the next step. The material was characterized by proton and mass spectroscopy.

EXAMPLE 4

Preparation of Compounds of Formula (1c)

Using the procedure set out in Example 3, but replacing the $R^1$Hal reactants, iodopropane with other halogenated derivatives; the following compounds of formula (1c) are prepared:
6-methyl-3-ethyl-1,3-dihydropyrimidine-2,4-dione;
3,6-dimethyl-1,3-dihydropyrimidine-2,4-dione;
6-methyl-3-methoxy-1,3-dihydropyrimidine-2,4-dione;
6-methyl-3-n-butyl-1,3-dihydropyrimidine-2,4-dione;
6-methyl-3-isobutyl-1,3-dihydropyrimidine-2,4-dione;
6-methyl-3-phenylethyl-1,3-dihydropyrimidine-2,4-dione;
6-methyl-3-cyclobutyl-1,3-dihydropyrimidine-2,4-dione;
6-methyl-3-(pyrid-4-ylmethyl)-1,3-dihydropyrimidine-2,4-dione;
6-methyl-3-(furan-3-ylmethyl)-1,3-dihydropyrimidine-2,4-dione;
6-methyl-3-(4-methoxybenzyl)-1,3-dihydropyrimidine-2,4-dione; and
6-methyl-3-(4-fluorobenzyl)-1,3-dihydropyrimidine-2,4-dione.

EXAMPLE 5

Preparation of a Compound of Formula (1e), 6-Methyl-5-nitro-3-propyl-1,3-dihydropyrimidine-2,4-dione

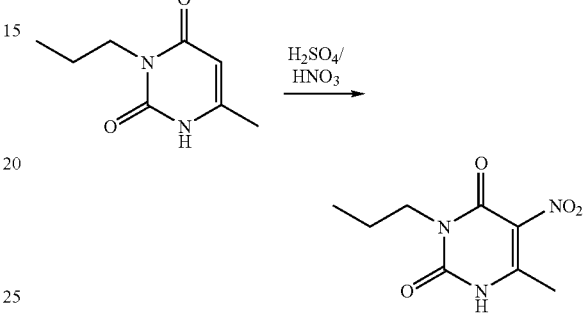

3-propyl-6-methyl-1,3-dihydropyrimidine-2,4-dione (3 g), as prepared in Example 3, was added to a solution of concentrated $H_2SO_4$ (12 ml) and $HNO_3$ (9.6 ml) at 0° C. The reaction mixture was allowed to come to room temperature and continued stirring for another 2 h. The reaction mixture was then poured into water and extracted with ethyl acetate (3×50 mL). The organic layer was washed with water, brine and dried over $Na_2SO_4$. Removal of the solvent and recrystallization of the residue with ethylacetate/hexane mixture furnished the 6-methyl-5-nitro-3-propyl-1,3-dihydropyrimidine-2,4-dione(1.56 g).

EXAMPLE 6

Preparation of Compounds of Formula (1e)

Using the procedure set out in Example 5, but replacing the 3-propyl-6-methyl-1,3-dihydropyrimidine-2,4-dione reactant with uracil compounds having other substituents in the $R^1$ position; the following compounds of formula (1e) are prepared:
6-methyl-5-nitro-3-ethyl-1,3-dihydropyrimidine-2,4-dione;
3,6-dimethyl-5-nitro-1,3-dihydropyrimidine-2,4-dione;
6-methyl-5-nitro-3-methoxy-1,3-dihydropyrimidine-2,4-dione;
6-methyl-5-nitro-3-n-butyl-1,3-dihydropyrimidine-2,4-dione;
6-methyl-5-nitro-3-isobutyl-1,3-dihydropyrimidine-2,4-dione;
6-methyl-5-nitro-3-phenylethyl-1,3-dihydropyrimidine-2,4-dione;
6-methyl-5-nitro-3-cyclobutyl-1,3-dihydropyrimidine-2,4-dione;
6-methyl-5-nitro-3-(pyrid-4-ylmethyl)-1,3-dihydropyrimidine-2,4-dione;
6-methyl-5-nitro-3-(furan-3-ylmethyl)-1,3-dihydropyrimidine-2,4-dione;
6-methyl-5-nitro-3-(4-methoxybenzyl)-1,3-dihydropyrimidine-2,4-dione; and 6-methyl-5-nitro-3-(4-fluorobenzyl)-1,3-dihydropyrimidine-2,4-dione.

EXAMPLE 7

Preparation of a Compound of Formula (1), 6-Methyl-5-nitro-1-ethyl-3-propyl-1,3-dihydropyrimidine-2,4-dione

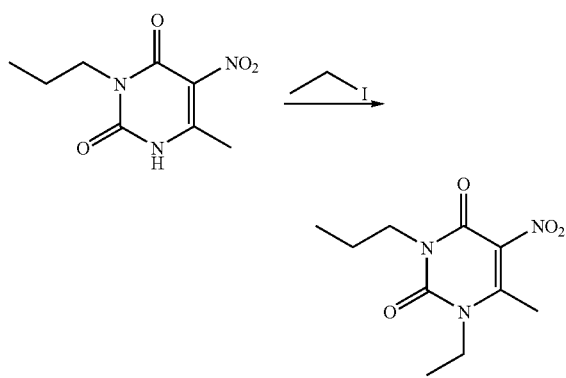

To a mixture of the nitro derivative, 6-methyl-5-nitro-3-propyl-1,3-dihydropyrimidine-2,4-dione prepared in Example 5 (1.56 g) and $K_2CO_3$ (3.0 g) in DMF was added iodoethane. The reaction mixture was heated at 80° C. for 3 h. After completion of the starting material, $K_2CO_3$ was filtered and DMF was distilled off. The residue was dissolved in ethyl acetate, washed with water, brine and dried over $Na_2SO_4$ Removal of solvent furnished the product as yellow oil, which was purified using flash chromatography. Elution with 30% ethyl acetate/hexane furnished the material as white solid, which was characterized by using NMR and mass.

EXAMPLE 8

Preparation of Compounds of Formula (1)

Using the procedure set out in Example 7, but replacing the iodoethane reactant with other alkylhalides; the following compounds of formula (1) are prepared:

1,6-dimethyl-5-nitro-3-ethyl-1,3-dihydropyrimidine-2,4-dione;
1,6-dimethyl-5-nitro-3-methoxy-1,3-dihydropyrimidine-2,4-dione;
1,6-dimethyl-5-nitro-3-n-butyl-1,3-dihydropyrimidine-2,4-dione;
1,6-dimethyl-5-nitro-3-isobutyl-1,3-dihydropyrimidine-2,4-dione;
1,6-dimethyl-5-nitro-3-phenylethyl-1,3-dihydropyrimidine-2,4-dione;
1,6-dimethyl-5-nitro-3-cyclobutyl-1,3-dihydropyrimidine-2,4-dione;
1,6-dimethyl-5-nitro-3-(pyrid-4-ylmethyl)-1,3-dihydropyrimidine-2,4-dione;
1,6-dimethyl-5-nitro-3-(furan-3-ylmethyl)-1,3-dihydropyrimidine-2,4-dione;
1,6-dimethyl-5-nitro-3-(4-methoxybenzyl)-1,3-dihydropyrimidine-2,4-dione;
1,6-dimethyl-5-nitro-3-(4-fluorobenzyl)-1,3-dihydropyrimidine-2,4-dione;
1,6-dimethyl-5-nitro-1-cyclopropyl methyl-3-ethyl-1,3-dihydropyrimidine-2,4-dione;
6-methyl-5-nitro-1-isobutyl-3-ethyl-1,3-dihydropyrimidine-2,4-dione;
1-isobutyl-3,6-dimethyl-5-nitro-1,3-dihydropyrimidine-2,4-dione;
1-isobutyl-6-methyl-5-nitro-3-methoxy-1,3-dihydropyrimidine-2,4-dione;
1-isobutyl-6-methyl-5-nitro-3-n-butyl-1,3-dihydropyrimidine-2,4-dione;
1-isobutyl-6-methyl-5-nitro-3-isobutyl-1,3-dihydropyrimidine-2,4-dione;
1-isobutyl-6-methyl-5-nitro-3-phenylethyl-1,3-dihydropyrimidine-2,4-dione;
1-isobutyl-6-methyl-5-nitro-3-cyclobutyl-1,3-dihydropyrimidine-2,4-dione;
1-isobutyl-6-methyl-5-nitro-3-(pyrid-4-ylmethyl)-1,3-dihydropyrimidine-2,4-dione;
1-isobutyl-6-methyl-5-nitro-3-(furan-3-ylmethyl)-1,3-dihydropyrimidine-2,4-dione;
1-isobutyl-6-methyl-5-nitro-3-(4-methoxybenzyl)-1,3-dihydropyrimidine-2,4-dione;
1-isobutyl-6-methyl-5-nitro-3-(4-fluorobenzyl)-1,3-dihydropyrimidine-2,4-dione;
6-methyl-5-nitro-1-cyclopropyl methyl-3-ethyl-1,3-dihydropyrimidine-2,4-dione;
1-cyclopropyl methyl-3,6-dimethyl-5-nitro-1,3-dihydropyrimidine-2,4-dione;
1-cyclopropyl methyl-6-methyl-5-nitro-3-methoxy-1,3-dihydropyrimidine-2,4-dione;
1-cyclopropyl methyl-6-methyl-5-nitro-3-n-butyl-1,3-dihydropyrimidine-2,4-dione;
1-cyclopropyl methyl-6-methyl-5-nitro-3-isobutyl-1,3-dihydropyrimidine-2,4-dione;
1-cyclopropyl methyl-6-methyl-5-nitro-3-phenylethyl-1,3-dihydropyrimidine-2,4-dione;
1-cyclopropyl methyl-6-methyl-5-nitro-3-cyclobutyl-1,3-dihydropyrimidine-2,4-dione;
1-cyclopropyl methyl-6-methyl-5-nitro-3-(pyrid-4-ylmethyl)-1,3-dihydropyrimidine-2,4-dione;
1-cyclopropyl methyl-6-methyl-5-nitro-3-(furan-3-ylmethyl)-1,3-dihydropyrimidine-2,4-dione;
1-cyclopropyl methyl-6-methyl-5-nitro-3-(4-methoxybenzyl)-1,3-dihydropyrimidine-2,4-dione; and
1-cyclopropyl methyl-6-methyl-5-nitro-3-(4-fluorobenzyl)-1,3-dihydropyrimidine-2,4-dione.

The N1-position was also substituted with methyl, isobutyl, and cyclopropyl methyl following the same procedure.

EXAMPLE 9

Preparation of a Compound of Formula (1)

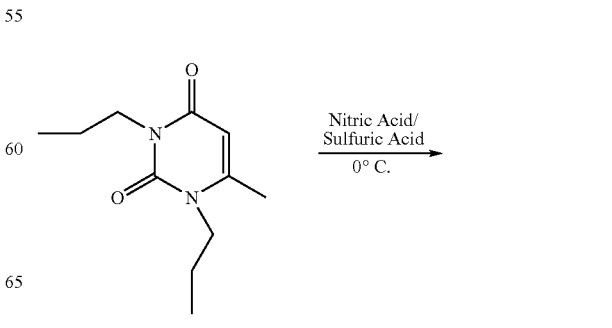

-continued

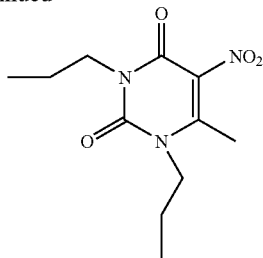

1.2 g, 6 mmol, of 6-methyl-1,3-dipropyl-1,3-dihydropyrimidine-2,4-dione, as prepared in Example 1, was added in small portions to a cooled (0° C.) solution of concentrated sulfuric acid (3.0 ml) and nitric acid (2.0 ml). The reaction stirred at 0° C. for 2 hours. The reaction mixture was poured over ice and a green amorphous solid formed. The solid was removed by filtration and washed copiously with water. The solid was dissolved in dichloromethane and concentrated. The residue was purified using column chromatography (1:1.2 EtOAc:Hexanes) to yield 6-methyl-5-nitro-1,3-dipropyl-1,3-dihydropyrimidine-2,4-dione(0.430 g, HNMR)

EXAMPLE 10

Preparation of Compounds of Formula (1)

Using the procedure set out in Example 9, but replacing the 6-methyl-1,3-dipropyl-1,3-dihydropyrimidine-2,4-dione with the various -1,3-dihydropyrimidine-2,4-diones prepared in Examples 2, 5, and 6, the following compounds of formula (1) are prepared:
1,3,6-triimethyl-5-nitro-1,3-dihydropyrimidine-2,4-dione;
6-methyl-5-nitro-1,3-diethyl-1,3-dihydropyrimidine-2,4-dione;
6-methyl-5-nitro-1,3-di(methoxyethyl)-1,3-dihydropyrimidine-2,4-dione;
6-methyl-1,3-di-n-butyl-5-nitro-1,3-dihydropyrimidine-2,4-dione;
6-methyl-1,3-diisobutyl-5-nitro-1,3-dihydropyrimidine-2,4-dione;
6-methyl-1,3-di(phenylethyl)-5-nitro-1,3-dihydropyrimidine-2,4-dione;
6-methyl-1,3-dicyclobutyl-5-nitro-1,3-dihydropyrimidine-2,4-dione;
6-methyl-1,3-di(pyrid-4-ylmethyl)-5-nitro-1,3-dihydropyrimidine-2,4-dione;
6-methyl-1,3-di(furan-3-ylmethyl)-5-nitro-1,3-dihydropyrimidine-2,4-dione;
6-methyl-1,3-di(4-methoxybenzyl)-5-nitro-1,3-dihydropyrimidine-2,4-dione;
6-methyl-1,3-di(4-trifluoromethylbenzyl)-5-nitro-1,3-dihydropyrimidine-2,4-dione;
6-methyl-1,3-di(fluorobenzyl)-5-nitro-1,3-dihydropyrimidine-2,4-dione;
1,6-dimethyl-3-ethyl-5-nitro-1,3-dihydropyrimidine-2,4-dione;
6-methyl-1-ethyl-3-propyl-5-nitro-1,3-dihydropyrimidine2,4-dione;
6-methyl-1-propyl-3-methoxyethyl-5-nitro-1,3-dihydropyrimidine2,4-dione;
6-methyl-1-methoxyethyl-3-n-butyl-5-nitro-1,3-dihydropyrimidine2,4-dione;
6-methyl-1-n-butyl-3-isobutyl-5-nitro-1,3-dihydropyrimidine2,4-dione;
6-methyl-1-isobutyl-3-phenylethyl-5-nitro-1,3-dihydropyrimidine2,4-dione;
6-methyl-1-phenylethyl-3-cyclobutyl-5-nitro-1,3-dihydropyrimidine2,4-dione;
6-methyl-1-cyclobutyl-3-(pyrid-4-ylmethyl)-5-nitro-1,3-dihydropyrimidine2,4-dione;
6-methyl-1-(pyrid-4-ylmethyl)-3-(furan-3-ylmethyl)-5-nitro-1,3-dihydropyrimidine2,4-dione;
6-methyl-1-(furan-3-ylmethyl)-3-(4-methoxybenzyl)-5-nitro-1,3-dihydropyrimidine2,4-dione; and
6-methyl-1-(4-methoxybenzyl)-3-(fluorobenxyl)-5-nitro-1,3-dihydropyrimidine2,4-dione.

EXAMPLE 11

Preparation of a Compound of Formula (2a)

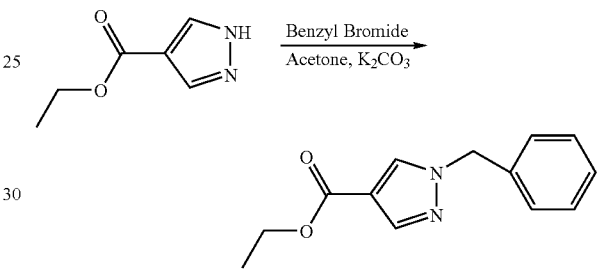

To a solution of Ethyl-4-pyrazole-carboxylate (14.0 g, 100 mmol) in Acetone (200 ml) was added potassium carbonate (27.6 g, 200 mmol) and Benzyl Bromide (12 ml, 100 mmol). The mixture was heated to 60° C. and stirred for 14 hours. The reaction mixture was cooled and filtered to remove any solids. The filtrate was concentrated and the residue was purified using column chromatography (3:1 Hexanes:Ethyl Acetate) to yield ethyl 1-benzylpyrazole-4-carboxylate (19.0 g, HNMR)

EXAMPLE 12

Preparation of Compounds of Formula (2a)

Using the procedure set out in Example 11, but replacing the benzyl bromide with other suitable bromides, the following compounds of formula (2a) are prepared:
ethyl 1-methylpyrazole-4-carboxylate;
ethyl 1-methylpyrrole-2-carboxylate;
ethyl 1-phenylpyrazole-4-carboxylate;
ethyl 1-(4-methylbenzyl)pyrazole-4-carboxylate;
ethyl 1-(3-methoxybenzyl)pyrazole-4-carboxylate;
ethyl 1-(2-trifluoromethylbenzyl)pyrazole-4-carboxylate;
ethyl 1-(2-fluorobenzyl)pyrazole-4-carboxylate;
ethyl 1-(3-trifluoromethylbenzyl)pyrazole-4-carboxylate;
ethyl 1-(3-fluorobenzyl)pyrazole-4-carboxylate;
ethyl 1-pyridin-4-yl-carboxylate;
ethyl 1-pyridin-2-yl-carboxylate;
ethyl 1-(5-(thiophene-2-yl)isoxazol-3-yl)-carboxylate; and
ethyl 1-(N-oxypyridin-4-yl)-carboxylate.

EXAMPLE 13

Preparation of a Compound of Formula (2b)

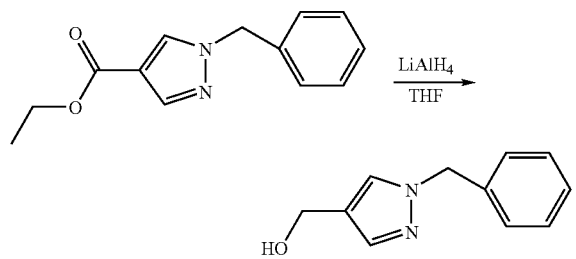

The ethyl 1-benzylpyrazole-4-carboxylate (5 g, 21.7 mmol) prepared in Example 9 was dissolved in THF (40 ml) and cooled to 0 degrees under inert atmosphere. Lithium Aluminum Hydride (1M in THF, 21.7 ml) was added dropwise. After complete addition, the solution was allowed to warm to room temperature and stirred for 2 hours. Saturated ammonium chloride solution was added slowly until gas evolution ceased. All solvent was removed in vacuo. To the residue was added 100 ml water and 250 ml ethyl acetate and placed in a separatory funnel. The organic layer was washed with water and concentrated to yield [1-benzylpyrazol-4-yl]methan-1-ol (3.8 g, HNMR)

EXAMPLE 14

Preparation of Compounds of Formula (2b)

Using the procedure set out in Example 11, but replacing the carboxylate with the various carboxylates prepared as described in Example 10, the following compounds of formula (2b) are prepared:
[1-methylpyrazol-4-yl]methan-1-ol;
[1-phenylpyrazol-4-yl]methan-1-ol;
[1-(4-methylbenzyl)pyrazol-4-yl]methan-1-ol;
[1-(3-methoxybenzyl)pyrazol-4-yl]methan-1-ol;
[1-(2-trifluoromethylbenzyl)pyrazol]-4-yl]methan-1-ol;
[1-(2-fluorobenzyl)pyrazol-4-yl]methan-1-ol; and
[1-(4-methylbenzyl)pyrazol-4-yl]methan-1-ol.

EXAMPLE 15

Preparation of a Compound of Formula (2)

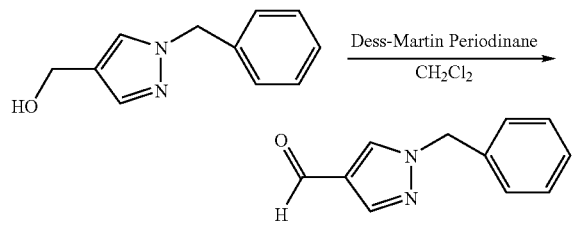

The [1-benzylpyrazol-4-yl]methan-1-ol prepared in Example 11 (0.376 g, 2.0 mmol) was placed in dichloromethane (10 ml) and added dropwise to a cooled solution (0° C.) of Dess-Martin Periodinane (1.27 g, 3.0 mmol) in dichloromethane (20 ml). The reaction was allowed to stir at room temperature for one hour and then concentrated. Diethyl ether (50 ml) was added and a white solid formed. The solid was removed by filtration and further washed with ether. The filtrate was concentrated and the residue dissolved in dichloromethane (50 ml). The organic layer was washed with saturated sodium bicarbonate (2×40 ml) and brine solution (20 ml) and concentrated to yield[1-benzylpyrazol-4-yl] formaldehyde (0.26 g).

EXAMPLE 16

Preparation of Compounds of Formula (2)

Using the procedure set out in Example 15, but replacing the carboxylate with the various alcohols prepared as described in Example 14, the following compounds of formula (2) are prepared:
[1-methylpyrazol-4-yl]formaldehyde;
[1-phenylpyrazol-4-yl]formaldehyde;
[1-(3-methoxybenzyl)pyrazol-4-yl]formaldehyde;
[1-(2-trifluoromethylbenzyl)pyrazol]-4-yl]formaldehyde;
[1-(2-fluorobenzyl)pyrazol-4-yl]formaldehyde; and
[1-(4-methylbenzyl)pyrazol-4-yl]formnaldehyde.

EXAMPLE 17

Preparation of a Compound of Formula (3)

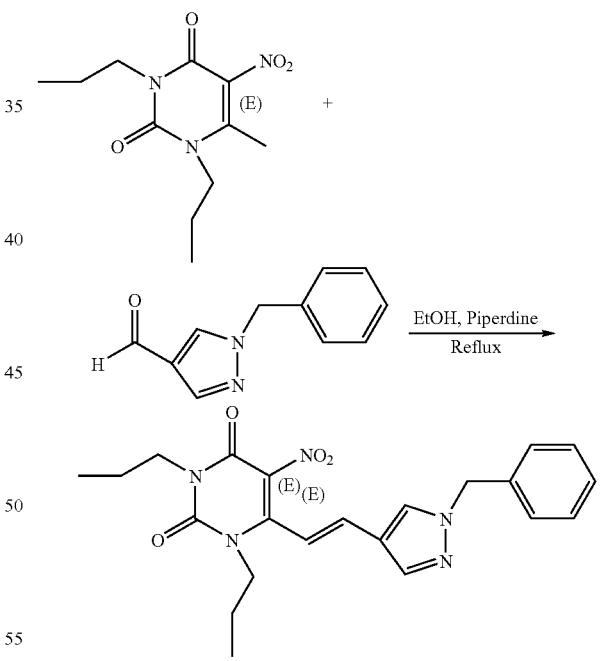

To a solution of the [1-benzylpyrazol-4-yl]formaldehyde prepared in Example 15 (0.26 g, 1.4 mmol) in ethanol (4 ml) was added piperdine (0.14 uL, 1.4 mmol) and 6-methyl-5-nitro-1,3-dipropyl-1,3-dihydropyrimidine-2,4-dione, as prepared in Example 9, (0.355 g, 1.4 mmol). The mixture was stirred and heated to reflux for 14 hours. The mixture was concentrated and purified using preparative thin layer chromatography (5% MeOH in Dichloromethane) to yield 6-{(1E)-2-[1-benzylpyrazol-4-yl]vinyl}-5-nitro-1,3-dipropyl-1,3-dihydropyrimidine-2,4-dione(0.24 g, M+1=424.01)

EXAMPLE 18

Preparation of Compounds of Formula (3)

Using the procedure set out in Example 17, but replacing the formaldehyde with the various formaldehydes prepared in Example 15 and/or replacing the nitro uracil with the various nitro uracil compounds prepared in Examples 7, 8, and 10, the following compounds of formula (3) are prepared 6-[1-methylpyrazol-4-yl]-1,3-diethyl-5-nitro-1,3-dihydropyrimidine-2,4-dione;
6-[1-methylpyrazol-4-yl]-1,3-di(methoxyethyl)-5-nitro-1,3-dihydropyrimidine-2,4-dione;
6-[1-methylpyrazol-4-yl]-1,3-di-n-butyl-5-nitro-1,3-dihydropyrimidine-2,4-dione;
6-[1-methylpyrazol-4-yl]-1,3-diisobutyl-5-nitro-1,3-dihydropyrimidine-2,4-dione;
6-[1-methylpyrazol-4-yl]-1,3-di(phenylethyl)-5-nitro-1,3-dihydropyrimidine-2,4-dione;
6-[1-methylpyrazol-4-yl]-1,3-dicyclobutyl-5-nitro-1,3-dihydropyrimidine-2,4-dione;
6-[1-methylpyrazol-4-yl]-1,3-di(pyrid-4-ylmethyl)-5-nitro-1,3-dihydropyrimidine-2,4-dione;
6-[1-methylpyrazol-4-yl]-1,3-di(furan-3-ylmethyl)-5-nitro-1,3-dihydropyrimidine-2,4-dione;
6-[1-methylpyrazol-4-yl]-1,3-di(4-methoxybenzyl)-5-nitro-1,3-dihydropyrimidine-2,4-dione;
6-[1-methylpyrazol-4-yl]-1,3-di(4-trifluoromethylbenzyl-5-nitro-1,3-dihydropyrimidine-2,4-dione;
6-[1-methylpyrazol-4-yl]-1,3-di(fluorobenzyl)-5-nitro-1,3-dihydropyrimidine-2,4-dione;
6-[1-methylpyrazol-4-yl]-1-ethyl-3-propyl-5-nitro-1,3-dihydropyrimidine-2,4-dione;
6-[1-methylpyrazol-4-yl]-1-propyl-3-methoxyethyl-5-nitro-1,3-dihydropyrimidine-2,4-dione;
6-[1-methylpyrazol-4-yl]-1-methoxyethyl-3-n-butyl-5-nitro-1,3-dihydropyrimidine-2,4-dione;
6-[1-methylpyrazol-4-yl]-1-n-butyl-3-isobutyl-5-nitro-1,3-dihydropyrimidine-2,4-dione;
6-[1-methylpyrazol-4-yl]-1-isobutyl-3-phenylethyl-5-nitro-1,3-dihydropyrimidine-2,4-dione;
6-[1-methylpyrazol-4-yl]-1-phenylethyl-3-cyclobutyl-5-nitro-1,3-dihydropyrimidine-2,4-dione;
6-[1-methylpyrazol-4-yl]-1-cyclobutyl-3-(pyrid-4-ylmethyl)-5-nitro-1,3-dihydropyrimidine-2,4-dione;
6-[1-methylpyrazol-4-yl]-1-(pyrid-4-ylmethyl)-3-(furan-3-ylmethyl)-5-nitro-1,3-dihydropyrimidine-2,4-dione;
6-[1-methylpyrazol-4-yl]-1-(furan-3-ylmethyl)-3-(4-methoxybenzyl)-5-nitro-1,3-dihydropyrimidine-2,4-dione;
6-[1-methylpyrazol-4-yl]-1-(4-methoxybenzyl)-3-(fluorobenzyl)-5-nitro-1,3-dihydropyrimidine-2,4-dione;
6-[1-phenylpyrazol-4-yl]-1,3-diethyl-5-nitro-1,3-dihydropyrimidine-2,4-dione;
6-[1-phenylpyrazol-4-yl]-1,3-di(methoxyethyl)-5-nitro-1,3-dihydropyrimidine-2,4-dione;
6-[1-phenylpyrazol-4-yl]-1,3-di-n-butyl-5-nitro-1,3-dihydropyrimidine-2,4-dione;
6-[1-phenylpyrazol-4-yl]-1,3-diisobutyl-5-nitro-1,3-dihydropyrimidine-2,4-dione;
6-[1-phenylpyrazol-4-yl]-1,3-di(phenylethyl)-5-nitro-1,3-dihydropyrimidine-2,4-dione;
6-[1-phenylpyrazol-4-yl]-1,3-dicyclobutyl-5-nitro-1,3-dihydropyrimidine-2,4-dione;
6-[1-phenylpyrazol-4-yl]-1,3-di(pyrid-4-ylmethyl)-5-nitro-1,3-dihydropyrimidine-2,4-dione;
6-[1-phenylpyrazol-4-yl]-1,3-di(furan-3-ylmethyl)-5-nitro-1,3-dihydropyrimidine-2,4-dione;
6-[1-phenylpyrazol-4-yl]-1,3-di(4-methoxybenzyl)-5-nitro-1,3-dihydropyrimidine-2,4-dione;
6-[1-phenylpyrazol-4-yl]-1,3-di(4-trifluoromethylbenzyl-5-nitro-1,3-dihydropyrimidine-2,4-dione;
6-[1-phenylpyrazol-4-yl]-1,3-di(fluorobenzyl)-5-nitro-1,3-dihydropyrimidine-2,4-dione;
6-[1-phenylpyrazol-4-yl]-1-ethyl-3-propyl-5-nitro-1,3-dihydropyrimidine-2,4-dione;
6-[1-phenylpyrazol-4-yl]-1-propyl-3-methoxyethyl-5-nitro-1,3-dihydropyrimidine-2,4-dione;
6-[1-phenylpyrazol-4-yl]-1-methoxyethyl-3-n-butyl-5-nitro-1,3-dihydropyrimidine-2,4-dione;
6-[1-phenylpyrazol-4-yl]-1-n-butyl-3-isobutyl-5-nitro-1,3-dihydropyrimidine-2,4-dione;
6-[1-phenylpyrazol-4-yl]-1-isobutyl-3-phenylethyl-5-nitro-1,3-dihydropyrimidine-2,4-dione;
6-[1-phenylpyrazol-4-yl]-1-phenylethyl-3-cyclobutyl-5-nitro-1,3-dihydropyrimidine-2,4-dione;
6-[1-phenylpyrazol-4-yl]-1-cyclobutyl-3-(pyrid-4-ylmethyl)-5-nitro-1,3-dihydropyrimidine-2,4-dione;
6-[1-phenylpyrazol-4-yl]-1-(pyrid-4-ylmethyl)-3-(furan-3-ylmethyl)-5-nitro-1,3-dihydropyrimidine-2,4-dione;
6-[1-phenylpyrazol-4-yl]-1-(furan-3-ylmethyl)-3-(4-methoxybenzyl)-5-nitro-1,3-dihydropyrimidine-2,4-dione;
6-[1-phenylpyrazol-4-yl]-1-(4-methoxybenzyl)-3-(fluorobenzyl)-5-nitro-1,3-dihydropyrimidine-2,4-dione;
6-[1-(2-trifluoromethylbenzyl)pyrazol]-4-yl]-1,3-diethyl-5-nitro-1,3-dihydropyrimidine-2,4-dione;
6-[1-(2-trifluoromethylbenzyl)pyrazol]-4-yl]-1,3-di(methoxyethyl)-5-nitro-1,3-dihydropyrimidine-2,4-dione;
6-[1-(2-trifluoromethylbenzyl)pyrazol]-4-yl]-1,3-di-n-butyl-5-nitro-1,3-dihydropyrimidine-2,4-dione;
6-[1-(2-trifluoromethylbenzyl)pyrazol]-4-yl]-1,3-diisobutyl-5-nitro-1,3-dihydropyrimidine-2,4-dione;
6-[1-(2-trifluoromethylbenzyl)pyrazol]-4-yl]-1,3-di(phenylethyl)-5-nitro-1,3-dihydropyrimidine-2,4-dione;
6-[1-(2-trifluoromethylbenzyl)pyrazol]-4-yl]-1,3-dicyclobutyl-5-nitro-1,3-dihydropyrimidine-2,4-dione;
6-[1-(2-trifluoromethylbenzyl)pyrazol]-4-yl]-1,3-di(pyrid-4-ylmethyl)-5-nitro-1,3-dihydropyrimidine-2,4-dione;
6-[1-(2-trifluoromethylbenzyl)pyrazol]-4-yl]-1,3-di(furan-3-ylmethyl)-5-nitro-1,3-dihydropyrimidine-2,4-dione;
6-[1-(2-trifluoromethylbenzyl)pyrazol]-4-yl]-1,3-di(4-methoxybenzyl)-5-nitro-1,3-dihydropyrimidine-2,4-dione;
6-[1-(2-trifluoromethylbenzyl)pyrazol]-4-yl]-1,3-di(4-trifluoromethylbenzyl-5-nitro-1,3-dihydropyrimidine-2,4-dione;
6-[1-(2-trifluoromethylbenzyl)pyrazol]-4-yl]-1,3-di(fluorobenzyl)-5-nitro-1,3-dihydropyrimidine-2,4-dione;
6-[1-(2-trifluoromethylbenzyl)pyrazol]-4-yl]-1-ethyl-3-propyl-5-nitro-1,3-dihydropyrimidine-2,4-dione;
6-[1-(2-trifluoromethylbenzyl)pyrazol]-4-yl]-1-propyl-3-methoxyethyl-5-nitro-1,3-dihydropyrimidine-2,4-dione;
6-[1-(2-trifluoromethylbenzyl)pyrazol]-4-yl]-1-methoxyethyl-3-n-butyl-5-nitro-1,3-dihydropyrimidine-2,4-dione;
6-[1-(2-trifluoromethylbenzyl)pyrazol]-4-yl]-1-n-butyl-3-isobutyl-5-nitro-1,3-dihydropyrimidine-2,4-dione;
6-[1-(2-trifluoromethylbenzyl)pyrazol]-4-yl]-1-isobutyl-3-phenylethyl-5-nitro-1,3-dihydropyrimidine-2,4-dione;
6-[1-(2-trifluoromethylbenzyl)pyrazol]-4-yl]-1-phenylethyl-3-cyclobutyl-5-nitro-1,3-dihydropyrimidine-2,4-dione;
6-[1-(2-trifluoromethylbenzyl)pyrazol]-4-yl]-1-cyclobutyl-3-(pyrid-4-ylmethyl)-5-nitro-1,3-dihydropyrimidine-2,4-dione;

6-[1-(2-trifluoromethylbenzyl)pyrazol]-4-yl]-1-(pyrid-4-yl-methyl)-3-(furan-3-ylmethyl)-5-nitro-1,3-dihydropyrimidine-2,4-dione;
6-[1-(2-trifluoromethylbenzyl)pyrazol]-4-yl]-1-(furan-3-ylmethyl)-3-(4-methoxybenzyl)-5-nitro-1,3-dihydropyrimidine-2,4-dione;
6-[1-(2-trifluoromethylbenzyl)pyrazol]-4-yl]-1-(4-methoxybenzyl)-3-(fluorobenzyl)-5-nitro-1,3-dihydropyrimidine-2,4-dione;
6-[1-(2-fluorobenzyl)pyrazol-4-yl]-1,3-diethyl-5-nitro-1,3-dihydropyrimidine-2,4-dione;
6-[1-(2-fluorobenzyl)pyrazol-4-yl]-1,3-di(methoxyethyl)-5-nitro-1,3-dihydropyrimidine-2,4-dione;
6-[1-(2-fluorobenzyl)pyrazol-4-yl]-1,3-di-n-butyl-5-nitro-1,3-dihydropyrimidine-2,4-dione;
6-[1-(2-fluorobenzyl)pyrazol-4-yl]-1,3-diisobutyl-5-nitro-1,3-dihydropyrimidine-2,4-dione;
6-[1-(2-fluorobenzyl)pyrazol-4-yl]-1,3-di(phenylethyl)-5-nitro-1,3-dihydropyrimidine-2,4-dione;
6-[1-(2-fluorobenzyl)pyrazol-4-yl]-1,3-dicyclobutyl-5-nitro-1,3-dihydropyrimidine-2,4-dione;
6-[1-(2-fluorobenzyl)pyrazol-4-yl]-1,3-di(pyrid-4-ylmethyl)-5-nitro-1,3-dihydropyrimidine-2,4-dione;
6-[1-(2-fluorobenzyl)pyrazol-4-yl]-1,3-di(furan-3-ylmethyl)-5-nitro-1,3-dihydropyrimidine-2,4-dione;
6-[1-(2-fluorobenzyl)pyrazol-4-yl]-1,3-di(4-methoxybenzyl)-5-nitro-1,3-dihydropyrimidine-2,4-dione;
6-[1-(2-fluorobenzyl)pyrazol-4-yl]-1,3-di(4-trifluoromethylbenzyl-5-nitro-1,3-dihydropyrimidine-2,4-dione;
6-[1-(2-fluorobenzyl)pyrazol-4-yl]-1,3-di(fluorobenzyl)-5-nitro-1,3-dihydropyrimidine-2,4-dione;
6-[1-(2-fluorobenzyl)pyrazol-4-yl]-1-ethyl-3-propyl-5-nitro-1,3-dihydropyrimidine-2,4-dione;
6-[1-(2-fluorobenzyl)pyrazol-4-yl]-1-propyl-3-methoxyethyl-5-nitro-1,3-dihydropyrimidine-2,4-dione;
6-[1-(2-fluorobenzyl)pyrazol-4-yl]-1-methoxyethyl-3-n-butyl-5-nitro-1,3-dihydropyrimidine-2,4-dione;
6-[1-(2-fluorobenzyl)pyrazol-4-yl]-1-n-butyl-3-isobutyl-5-nitro-1,3-dihydropyrimidine-2,4-dione;
6-[1-(2-fluorobenzyl)pyrazol-4-yl]-1-isobutyl-3-phenylethyl-5-nitro-1,3-dihydropyrimidine-2,4-dione;
6-[1-(2-fluorobenzyl)pyrazol-4-yl]-1-phenylethyl-3-cyclobutyl-5-nitro-1,3-dihydropyrimidine-2,4-dione;
6-[1-(2-fluorobenzyl)pyrazol-4-yl]-1-cyclobutyl-3-(pyrid-4-ylmethyl)-5-nitro-1,3-dihydropyrimidine-2,4-dione;
6-[1-(2-fluorobenzyl)pyrazol-4-yl]-1-(pyrid-4-ylmethyl)-3-(furan-3-ylmethyl)-5-nitro-1,3-dihydropyrimidine-2,4-dione;
6-[1-(2-fluorobenzyl)pyrazol-4-yl]-1-(furan-3-ylmethyl)-3-(4-methoxybenzyl)-5-nitro-1,3-dihydropyrimidine-2,4-dione; and
6-[1-(2-fluorobenzyl)pyrazol-4-yl]-1-(4-methoxybenzyl)-3-(fluorobenzyl)-5-nitro-1,3-dihydropyrimidine-2,4-dione.

EXAMPLE 19

Preparation of Compounds of Formula (4)

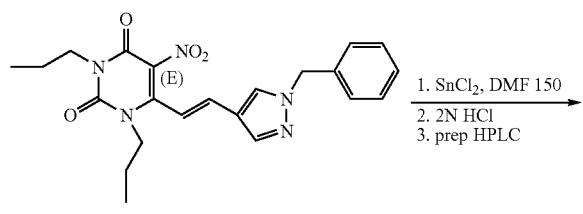

-continued

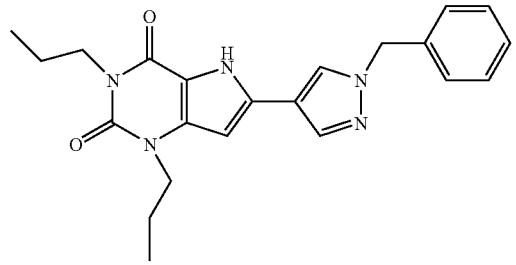

To a solution of 6-{(1E)-2-[1-benzylpyrazol-4-yl]vinyl}-5-nitro-1,3-dipropyl-1,3-dihydropyrimidine-2,4-dione prepared in Example 18 (0.24 g, 0.57 mmol) in N,N'-dimethyl formamide (4 ml) was added tin (II) chloride (1.07 g, 5.7 mmol). The reaction mixture was heated to 150° for 2 hours. After cooling to room temperature 2N HCl (6 ml) was added and a light brown precipitate formed and was removed by filtration and washed with water (5 ml). The precipitate (0,025 g) was dissolved in DMSO (0.5 ml) and purified using preparative HPLC to yield 6-[1-benzylpyrazol-4-yl]-1,3-dipropyl-1,3-dihydropyrrolo[3,2-d]pyrimidine-2,4-dione, (0.009 g, M+1=392.2)

EXAMPLE 20

Preparation of Compounds of Formula (4)

Using the procedure set out in Example 19, but replacing the 5-nitro-1,3-dihydropyrimidine-2,4-dione with the various diones prepared in Example 18, the following compounds of formula (4) are prepared:
6-[1-methylpyrazol-4-yl]-1,3-diethyl-1,3-dihydropyrrolo[3,2-d]pyrimidine-2,4-dione;
6-[1-methylpyrazol-4-yl]-1,3-di(methoxyethyl)-1,3-dihydropyrrolo[3,2-d]pyrimidine-2,4-dione;
6-[1-methylpyrazol-4-yl]-1,3-di-n-butyl-1,3-dihydropyrrolo[3,2-d]pyrimidine-2,4-dione;
6-[1-methylpyrazol-4-yl]-1,3-diisobutyl-1,3-dihydropyrrolo[3,2-d]pyrimidine-2,4-dione;
6-[1-methylpyrazol-4-yl]-1,3-di(phenylethyl)-1,3-dihydropyrrolo[3,2-d]pyrimidine-2,4-dione;
6-[1-methylpyrazol-4-yl]-1,3-dicyclobutyl-1,3-dihydropyrrolo[3,2-d]pyrimidine-2,4-dione;
6-[1-methylpyrazol-4-yl]-1,3-di(pyrid-4-ylmethyl)-1,3-dihydropyrrolo[3,2-d]pyrimidine-2,4-dione;
6-[1-methylpyrazol-4-yl]-1,3-di(furan-3-ylmethyl)-1,3-dihydropyrrolo[3,2-d]pyrimidine-2,4-dione;
6-[1-methylpyrazol-4-yl]-1,3-di(4-methoxybenzyl)-1,3-dihydropyrrolo[3,2-d]pyrimidine-2,4-dione;
6-[1-methylpyrazol-4-yl]-1,3-di(4-trifluoromethylbenzyl-1,3-dihydropyrrolo[3,2-d]pyrimidine-2,4-dione;
6-[1-methylpyrazol-4-yl]-1,3-di(fluorobenzyl)-1,3-dihydropyrrolo[3,2-d]pyrimidine-2,4-dione;
6-[1-methylpyrazol-4-yl]-1-ethyl-3-propyl-1,3-dihydropyrrolo[3,2-d]pyrimidine-2,4-dione;
6-[1-methylpyrazol-4-yl]-1-propyl-3-methoxyethyl-1,3-dihydropyrrolo[3,2-d]pyrimidine-2,4-dione;
6-[1-methylpyrazol-4-yl]-1-methoxyethyl-3-n-butyl-1,3-dihydropyrrolo[3,2-d]pyrimidine-2,4-dione;
6-[1-methylpyrazol-4-yl]-1-n-butyl-3-isobutyl-1,3-dihydropyrrolo[3,2-d]pyrimidine-2,4-dione;
6-[1-methylpyrazol-4-yl]-1-isobutyl-3-phenylethyl-1,3-dihydropyrrolo[3,2-d]pyrimidine-2,4-dione;

6-[1-methylpyrazol-4-yl]-1-phenylethyl-3-cyclobutyl-1,3-dihydropyrrolo[3,2-d]pyrimidine-2,4-dione;
6-[1-methylpyrazol-4-yl]-1-cyclobutyl-3-(pyrid-4-ylmethyl)-1,3-dihydropyrrolo[3,2-d]pyrimidine-2,4-dione;
6-[1-methylpyrazol-4-yl]-1-(pyrid-4-ylmethyl)-3-(furan-3-ylmethyl)-1,3-dihydropyrrolo[3,2-d]pyrimidine-2,4-dione;
6-[1-methylpyrazol-4-yl]-1-(furan-3-ylmethyl)-3-(4-methoxybenzyl)-1,3-dihydropyrrolo[3,2-d]pyrimidine-2,4-dione;
6-[1-methylpyrazol-4-yl]-1-(4-methoxybenzyl)-3-(fluorobenzyl)-1,3-dihydropyrrolo[3,2-d]pyrimidine-2,4-dione;
6-[1-phenylpyrazol-4-yl]-1,3-diethyl-1,3-dihydropyrrolo[3,2-d]pyrimidine-2,4-dione;
6-[1-phenylpyrazol-4-yl]-1,3-di(methoxyethyl)-1,3-dihydropyrrolo[3,2-d]pyrimidine-2,4-dione;
6-[1-phenylpyrazol-4-yl]-1,3-di-n-butyl-1,3-dihydropyrrolo[3,2-d]pyrimidine-2,4-dione;
6-[1-phenylpyrazol-4-yl]-1,3-diisobutyl-1,3-dihydropyrrolo[3,2-d]pyrimidine-2,4-dione;
6-[1-phenylpyrazol-4-yl]-1,3-di(phenylethyl)-1,3-dihydropyrrolo[3,2-d]pyrimidine-2,4-dione;
6-[1-phenylpyrazol-4-yl]-1,3-dicyclobutyl-1,3-dihydropyrrolo[3,2-d]pyrimidine-2,4-dione;
6-[1-phenylpyrazol-4-yl]-1,3-di(pyrid-4-ylmethyl)-1,3-dihydropyrrolo[3,2-d]pyrimidine-2,4-dione;
6-[1-phenylpyrazol-4-yl]-1,3-di(furan-3-ylmethyl)-1,3-dihydropyrrolo[3,2-d]pyrimidine-2,4-dione;
6-[1-phenylpyrazol-4-yl]-1,3-di(4-methoxybenzyl)-1,3-dihydropyrrolo[3,2-d]pyrimidine-2,4-dione;
6-[1-phenylpyrazol-4-yl]-1,3-di(4-trifluoromethylbenzyl-1,3-dihydropyrrolo[3,2-d]pyrimidine-2,4-dione;
6-[1-phenylpyrazol-4-yl]-1,3-di(fluorobenzyl)-1,3-dihydropyrrolo[3,2-d]pyrimidine-2,4-dione;
6-[1-phenylpyrazol-4-yl]-1-ethyl-3-propyl-1,3-dihydropyrrolo[3,2-d]pyrimidine-2,4-dione;
6-[1-phenylpyrazol-4-yl]-1-propyl-3-methoxyethyl-1,3-dihydropyrrolo[3,2-d]pyrimidine-2,4-dione;
6-[1-phenylpyrazol-4-yl]-1-methoxyethyl-3-n-butyl-1,3-dihydropyrrolo[3,2-d]pyrimidine-2,4-dione;
6-[1-phenylpyrazol-4-yl]-1-n-butyl-3-isobutyl-1,3-dihydropyrrolo[3,2-d]pyrimidine-2,4-dione;
6-[1-phenylpyrazol-4-yl]-1-isobutyl-3-phenylethyl-1,3-dihydropyrrolo[3,2-d]pyrimidine-2,4-dione;
6-[1-phenylpyrazol-4-yl]-1-phenylethyl-3-cyclobutyl-1,3-dihydropyrrolo[3,2-d]pyrimidine-2,4-dione;
6-[1-phenylpyrazol-4-yl]-1-cyclobutyl-3-(pyrid-4-ylmethyl)-1,3-dihydropyrrolo[3,2-d]pyrimidine-2,4-dione;
6-[1-phenylpyrazol-4-yl]-1-(pyrid-4-ylmethyl)-3-(furan-3-ylmethyl)-1,3-dihydropyrrolo[3,2-d]pyrimidine-2,4-dione;
6-[1-phenylpyrazol-4-yl]-1-(furan-3-ylmethyl)-3-(4-methoxybenzyl)-1,3-dihydropyrrolo[3,2-d]pyrimidine-2,4-dione;
6-[1-phenylpyrazol-4-yl]-1-(4-methoxybenzyl)-3-(fluorobenzyl)-1,3-dihydropyrrolo[3,2-d]pyrimidine-2,4-dione;
6-[1-(2-trifluoromethylbenzyl)pyrazol]-4-yl]-1,3-diethyl-1,3-dihydropyrrolo[3,2-d]pyrimidine-2,4-dione;
6-[1-(2-trifluoromethylbenzyl)pyrazol]-4-yl]-1,3-di(methoxyethyl)-1,3-dihydropyrrolo[3,2-d]pyrimidine-2,4-dione;
6-[1-(2-trifluoromethylbenzyl)pyrazol]-4-yl]-1,3-di-n-butyl-1,3-dihydropyrrolo[3,2-d]pyrimidine-2,4-dione;
6-[1-(2-trifluoromethylbenzyl)pyrazol]-4-yl]-1,3-diisobutyl-1,3-dihydropyrrolo[3,2-d]pyrimidine-2,4-dione;
6-[1-(2-trifluoromethylbenzyl)pyrazol]-4-yl]-1,3-di(phenylethyl)-1,3-dihydropyrrolo[3,2-d]pyrimidine-2,4-dione;
6-[1-(2-trifluoromethylbenzyl)pyrazol]-4-yl]-1,3-dicyclobutyl-1,3-dihydropyrrolo[3,2-d]pyrimidine-2,4-dione;
6-[1-(2-trifluoromethylbenzyl)pyrazol]-4-yl]-1,3-di(pyrid-4-ylmethyl)-1,3-dihydropyrrolo[3,2-d]pyrimidine-2,4-dione;
6-[1-(2-trifluoromethylbenzyl)pyrazol]-4-yl]-1,3-di(furan-3-ylmethyl)-1,3-dihydropyrrolo[3,2-d]pyrimidine-2,4-dione;
6-[1-(2-trifluoromethylbenzyl)pyrazol]-4-yl]-1,3-di(4-methoxybenzyl)-1,3-dihydropyrrolo[3,2-d]pyrimidine-2,4-dione;
6-[1-(2-trifluoromethylbenzyl)pyrazol]-4-yl]-1,3-di(4-trifluoromethylbenzyl-1,3-dihydropyrrolo[3,2-d]pyrimidine-2,4-dione;
6-[1-(2-trifluoromethylbenzyl)pyrazol]-4-yl]-1,3-di(fluorobenzyl)-1,3-dihydropyrrolo[3,2-d]pyrimidine-2,4-dione;
6-[1-(2-trifluoromethylbenzyl)pyrazol]-4-yl]-1-ethyl-3-propyl-1,3-dihydropyrrolo[3,2-d]pyrimidine-2,4-dione;
6-[1-(2-trifluoromethylbenzyl)pyrazol]-4-yl]-1-propyl-3-methoxyethyl-1,3-dihydropyrrolo[3,2-d]pyrimidine-2,4-dione;
6-[1-(2-trifluoromethylbenzyl)pyrazol]-4-yl]-1-methoxyethyl-3-n-butyl-1,3-dihydropyrrolo[3,2-d]pyrimidine-2,4-dione;
6-[1-(2-trifluoromethylbenzyl)pyrazol]-4-yl]-1-n-butyl-3-isobutyl-1,3-dihydropyrrolo[3,2-d]pyrimidine-2,4-dione;
6-[1-(2-trifluoromethylbenzyl)pyrazol]-4-yl]-1-isobutyl-3-phenylethyl-1,3-dihydropyrrolo[3,2-d]pyrimidine-2,4-dione;
6-[1-(2-trifluoromethylbenzyl)pyrazol]-4-yl]-1-phenylethyl-3-cyclobutyl-1,3-dihydropyrrolo[3,2-d]pyrimidine-2,4-dione;
6-[1-(2-trifluoromethylbenzyl)pyrazol]-4-yl]-1-cyclobutyl-3-(pyrid-4-ylmethyl)-1,3-dihydropyrrolo[3,2-d]pyrimidine-2,4-dione;
6-[1-(2-trifluoromethylbenzyl)pyrazol]-4-yl]-1-(pyrid-4-ylmethyl)-3-(furan-3-ylmethyl)-1,3-dihydropyrrolo[3,2-d]pyrimidine-2,4-dione;
6-[1-(2-trifluoromethylbenzyl)pyrazol]-4-yl]-1-(furan-3-ylmethyl)-3-(4-methoxybenzyl)-1,3-dihydropyrrolo[3,2-d]pyrimidine-2,4-dione;
6-[1-(2-trifluoromethylbenzyl)pyrazol]-4-yl]-1-(4-methoxybenzyl)-3-(fluorobenzyl)-1,3-dihydropyrrolo[3,2-d]pyrimidine-2,4-dione;
6-[1-(2-fluorobenzyl)pyrazol-4-yl]-1,3-diethyl-1,3-dihydropyrrolo[3,2-d]pyrimidine-2,4-dione;
6-[1-(2-fluorobenzyl)pyrazol-4-yl]-1,3-di(methoxyethyl)-1,3-dihydropyrrolo[3,2-d]pyrimidine-2,4-dione;
6-[1-(2-fluorobenzyl)pyrazol-4-yl]-1,3-di-n-butyl-1,3-dihydropyrrolo[3,2-d]pyrimidine-2,4-dione;
6-[1-(2-fluorobenzyl)pyrazol-4-yl]-1,3-diisobutyl-1,3-dihydropyrrolo[3,2-d]pyrimidine-2,4-dione;
6-[1-(2-fluorobenzyl)pyrazol-4-yl]-1,3-di(phenylethyl)-1,3-dihydropyrrolo[3,2-d]pyrimidine-2,4-dione;
6-[1-(2-fluorobenzyl)pyrazol-4-yl]-1,3-dicyclobutyl-1,3-dihydropyrrolo[3,2-d]pyrimidine-2,4-dione;
6-[1-(2-fluorobenzyl)pyrazol-4-yl]-1,3-di(pyrid-4-ylmethyl)-1,3-dihydropyrrolo[3,2-d]pyrimidine-2,4-dione;
6-[1-(2-fluorobenzyl)pyrazol-4-yl]-1,3-di(furan-3-ylmethyl)-1,3-dihydropyrrolo[3,2-d]pyrimidine-2,4-dione;
6-[1-(2-fluorobenzyl)pyrazol-4-yl]-1,3-di(4-methoxybenzyl)-1,3-dihydropyrrolo[3,2-d]pyrimidine-2,4-dione;
6-[1-(2-fluorobenzyl)pyrazol-4-yl]-1,3-di(4-trifluoromethylbenzyl-1,3-dihydropyrrolo[3,2-d]pyrimidine-2,4-dione;
6-[1-(2-fluorobenzyl)pyrazol-4-yl]-1,3-di(fluorobenzyl)-1,3-dihydropyrrolo[3,2-d]pyrimidine-2,4-dione;
6-[1-(2-fluorobenzyl)pyrazol-4-yl]-1-ethyl-3-propyl-1,3-dihydropyrrolo[3,2-d]pyrimidine-2,4-dione;

6-[1-(2-fluorobenzyl)pyrazol-4-yl]-1-propyl-3-methoxy-ethyl-1,3-dihydropyrrolo[3,2-d]pyrimidine-2,4-dione;
6-[1-(2-fluorobenzyl)pyrazol-4-yl]-1-methoxyethyl-3-n-butyl-1,3-dihydropyrrolo[3,2-d]pyrimidine-2,4-dione;
6-[1-(2-fluorobenzyl)pyrazol-4-yl]-1-n-butyl-3-isobutyl-1,3-dihydropyrrolo[3,2-d]pyrimidine-2,4-dione;
6-[1-(2-fluorobenzyl)pyrazol-4-yl]-1-isobutyl-3-phenylethyl-1,3-dihydropyrrolo[3,2-d]pyrimidine-2,4-dione;
6-[1-(2-fluorobenzyl)pyrazol-4-yl]-1-phenylethyl-3-cyclobutyl-1,3-dihydropyrrolo[3,2-d]pyrimidine-2,4-dione;
6-[1-(2-fluorobenzyl)pyrazol-4-yl]-1-cyclobutyl-3-(pyrid-4-ylmethyl)-1,3-dihydropyrrolo[3,2-d]pyrimidine-2,4-dione;
6-[1-(2-fluorobenzyl)pyrazol-4-yl]-1-(pyrid-4-ylmethyl)-3-(furan-3-ylmethyl)-1,3-dihydropyrrolo[3,2-d]pyrimidine-2,4-dione;
6-[1-(2-fluorobenzyl)pyrazol-4-yl]-1-(furan-3-ylmethyl)-3-(4-methoxybenzyl)-1,3-dihydropyrrolo[3,2-d]pyrimidine-2,4-dione; and
6-[1-(2-fluorobenzyl)pyrazol-4-yl]-1-(4-methoxybenzyl)-3-(fluorobenzyl)-1,3-dihydropyrrolo[3,2-d]pyrimidine-2,4-dione.

EXAMPLE 21

Preparation of a Compound of Formula (I) where $R^1$ and $R^2$ are Propyl, $R^3$ is Hydrogen, and $R^4$ is 1-Methyl-1H-Pyrrol-2-yl

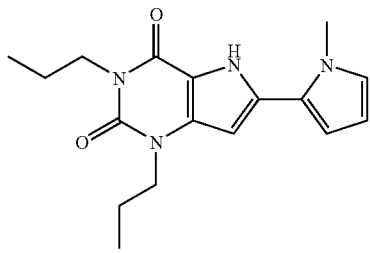

Using the procedures described in Examples 17 and 19, 6-methyl-5-nitro-1,3-dipropyl-1,3-dihydropyrimidine-2,4-dione as prepared in Example 9 was reacted with[1-methyl-1H-pyrrol-2-yl]formaldehyde prepared according to the procedures described in Examples 11, 13, and 15 to provide the aforementioned compound, namely, 8-(1-methyl-1H-pyrrol-2-yl)-1,3-dipropyl-1H-pyrrolo[3,2-d]pyrimidine-2,6-dione (M+1=314.98).

EXAMPLE 22

Preparation of a Compound of Formula (I) where $R^1$ and $R^2$ are Propyl, $R^3$ is Hydrogen, and $R^4$ is 1-(3-(Trifluoromethyl)Benzyl)-1H-Pyrazol-4-yl

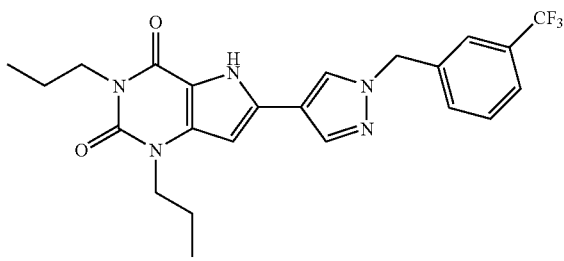

Using the procedures described in Examples 17 and 19, 6-methyl-5-nitro-1,3-dipropyl-1,3-dihydropyrimidine-2,4-dione from Example 9 was reacted with[1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-1,3-dipropyl-1H-pyrrolo [3,2-d]pyrimidine-2,6-dione. (M+1=460.01)

EXAMPLE 23

Preparation of a Compound of Formula (I) where $R^1$ and $R^2$ are Propyl, $R^3$ is Hydroxy, and $R^4$ is 1-Benzyl-1H-Pyrazol-4-yl

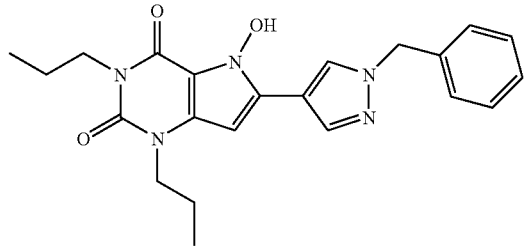

Using the procedures described in Examples 17 and 19, 6-methyl-5-nitro-1,3-dipropyl-1,3-dihydropyrimidine-2,4-dione from Example 9 was reacted with[1-benzylpyrazol-4-yl]formaldehyde prepared according to the procedures described in Examples 11, 13, and 15 to provide the aforementioned compound, namely, 8-(1-benzyl-1H-pyrazol-4-yl)-7-hydroxy-1,3-dipropyl-1H-pyrrolo[3,2-d]pyrimidine-2,6-dione (M+1=408.2).

EXAMPLE 24

Preparation of a Compound of Formula (I) where $R^1$ and $R^2$ are Propyl, $R^3$ is Hydrogen, and $R^4$ is 1-(3-FluoroBenzyl)-1H-Pyrazol-4-yl

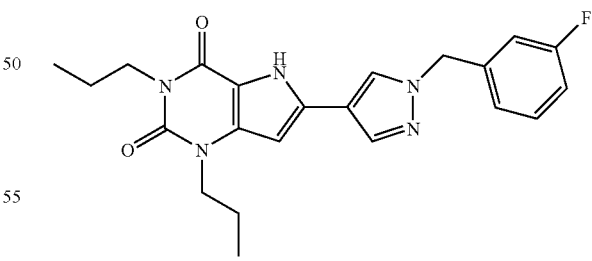

Using the procedures described in Examples 17 and 19, 6-methyl-5-nitro-1,3-dipropyl-1,3-dihydropyrimidine-2,4-dione from Example 9 was reacted with [1-(3-fluorobenzyl)-1H-pyrazol-4-yl]formaldehyde prepared according to the procedures described in Examples 11, 13, and 15 to provide the aforementioned compound, namely, 8-(1-(3-fluorobenzyl)-1H-pyrazol-4-yl)-1,3-dipropyl-1H-pyrrolo[3,2-d]pyrimidine-2,6-dione. (M+1=407.96)

EXAMPLE 25

Preparation of a Compound of Formula (I) where $R^1$ and $R^2$ are Propyl, $R^3$ is Hydroxy, and $R^4$ is Pyridin-4-yl

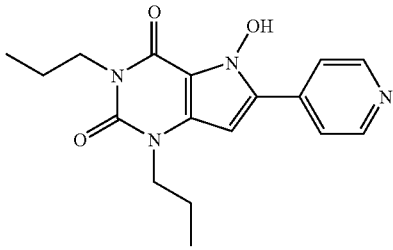

Using the procedures described in Examples 17 and 19, 6-methyl-5-nitro-1,3-dipropyl-1,3-dihydropyrimidine-2,4-dione from Example 9 was reacted with pyridin-4-yl-formaldehyde prepared according to the procedures described in Examples 11, 13, and 15 to provide the aforementioned compound, namely, 8-(pyridin-4-yl)-7-hydroxy-1,3-dipropyl-1H-pyrrolo[3,2-d]pyrimidine-2,6-dione. (M+1=328.94)

EXAMPLE 26

Preparation of a Compound of Formula (I) where $R^1$ and $R^2$ are Propyl, $R^3$ is Hydroxy, and $R^4$ is Pyridin-2-yl

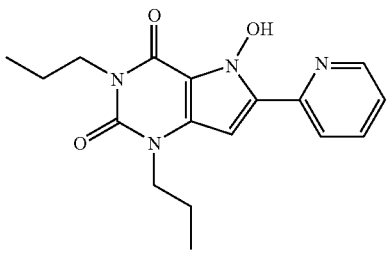

Using the procedures described in Examples 17 and 19, 6-methyl-5-nitro-1,3-dipropyl-1,3-dihydropyrimidine-2,4-dione from Example 9 was reacted with pyridin-2-yl-formaldehyde prepared according to the procedures described in Examples 11, 13, and 15 to provide the aforementioned compound, namely, 8-(pyridin-4-yl)-7-hydroxy-1,3-dipropyl-1H-pyrrolo[3,2-d]pyrimidine-2,6-dione. (M+1=327.99)

EXAMPLE 27

Preparation of a Compound of Formula (I) where $R^1$ and $R^2$ are Propyl, $R^3$ is Hydrogen, and $R^4$ is 5-(Thiophen-2-yl)Isoxazol-3-yl

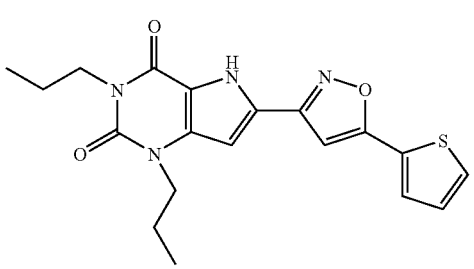

Using the procedures described in Examples 17 and 19, 6-methyl-5-nitro-1,3-dipropyl-1,3-dihydropyrimidine-2,4-dione as prepared in Example 9 was reacted with[5-(thiophen-2-yl)isoxazol-3-yl]formaldehyde prepared according to the procedures described in Examples 11, 13, and 15 to provide the aforementioned compound, namely, 8-(5-(thiophen-2-yl)isoxazol-3-yl)-1,3-dipropyl-1H-pyrrolo[3,2-d]pyrimidine-2,6-dione. (M+1=384.93)

EXAMPLE 28

Preparation of a Compound of Formula (I) where $R^1$ and $R^2$ are Propyl, $R^3$ is Hydroxy, and $R^4$ is 1-(3-(Trifluoromethyl)Benzyl)-1H-Pyrazol-4-yl

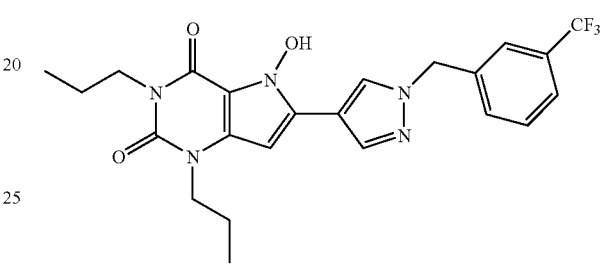

Using the procedures described in Examples 17 and 19, 6-methyl-5-nitro-1,3-dipropyl-1,3-dihydropyrimidine-2,4-dione from Example 9 was reacted with [1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-7-hydroxy-1,3-dipropyl-1H-pyrrolo[3,2-d]pyrimidine-2,6-dione. (M+1=475.72)

EXAMPLE 29

Preparation of a Compound of Formula (I) where $R^1$ and $R^2$ are Propyl, $R^3$ is Hydrogen, and $R^4$ is N-Oxypyridin-4-yl

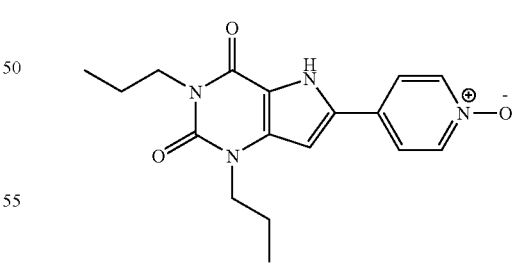

Using the procedures described in Examples 17 and 19, 6-methyl-5-nitro-1,3-dipropyl-1,3-dihydropyrimidine-2,4-dione from Example 9 was reacted with N-oxypyridin-4-yl-formaldehyde prepared according to the procedures described in Examples 11, 13, and 15 to provide the aforementioned compound, namely, 8-(N-oxypyridin-4-yl)-1,3-dipropyl-1H-pyrrolo[3,2-d]pyrimidine-2,6-dione. (M+1=329)

EXAMPLE 30

Preparation of a Compound of Formula (I) where $R^1$ is Propyl, $R^2$ is Ethyl, $R^3$ is Hydrogen, and $R^4$ is 1-(3-(Trifluoromethyl)Benzyl)-1H-Pyrazol-4-yl

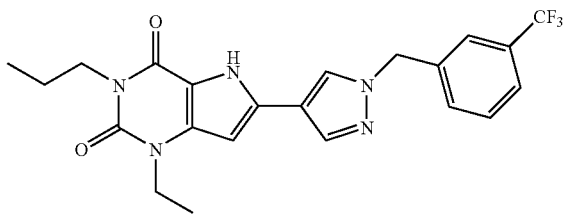

Using the procedures described in Examples 17 and 19, 6-methyl-5-nitro-1-ethyl-3-propyl-1,3-dihydropyrimidine-2,4-dione from Example 7 was reacted with [1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-1-ethyl-3-propyl-1H-pyrrolo[3,2-d]pyrimidine-2,6-dione. (M+1=446.0)

EXAMPLE 31

Preparation of a Compound of Formula (I) where $R^1$ is Propyl, $R^2$ is Methyl, $R^3$ is Hydrogen, and $R^4$ is 1-(3-(Trifluoromethyl)Benzyl)-1H-Pyrazol-4-yl

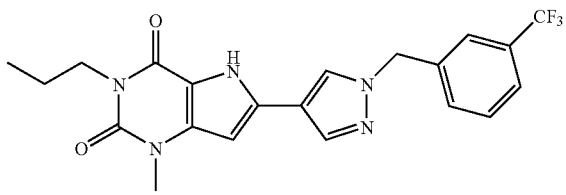

Using the procedures described in Examples 17 and 19, 1-6-dimethyl-5-nitro-3-propyl -1,3-dihydropyrimidine-2,4-dione, prepared as described in Example 7, was reacted with [1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-1-methyl-3-propyl-1H-pyrrolo[3,2-d]pyrimidine-2,6-dione.

EXAMPLE 32

Preparation of a Compound of Formula (I) where $R^1$ is Propyl, $R^2$ is Cyclopropylmethyl, $R^3$ is Hydrogen, and $R^4$ is 1-(3-(Trifluoromethyl)Benzyl)-1H-Pyrazol-4-yl

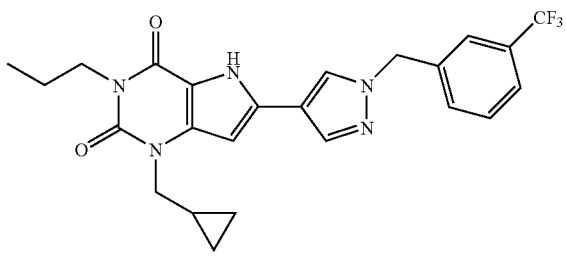

Using the procedures described in Examples 17 and 19, 6-methyl-5-nitro-1-cyclopropylmethyl-3-propyl-1,3-dihydropyrimidine-2,4-dione, prepared as described in Example 7, was reacted with [1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-1-cyclopropylmethyl -3-propyl-1H-pyrrolo[3,2-d]pyrimidine-2,6-dione.

EXAMPLE 33

Preparation of a Compound of Formula (I) where $R^1$ is Propyl, $R^2$ is Cyclopropylmethyl, $R^3$ is Hydrogen, and $R^4$ is 1-(3-(Trifluoromethyl)Benzyl)-1H-Pyrazol-4-yl

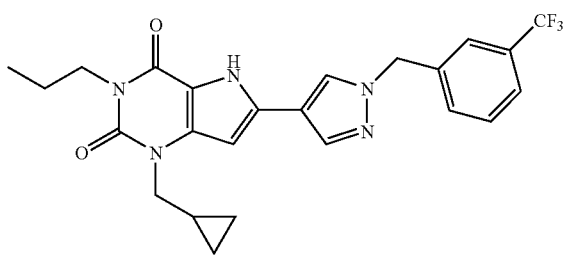

Using the procedures described in Examples 17 and 19, 6-methyl-5-nitro-1-isobutyl-3-propyl-1,3-dihydropyrimidine-2,4-dione, prepared as described in Example 7, was reacted with [1-(3-(trifluoromethyl)benzyl)-1H-pyrazol-4-yl]formaldehyde prepared according to the procedures described in Examples 11, 13, and 15 to provide the aforementioned compound, namely, 8-(1-(3-(trifluoromethyl)benzyl)-1H-pyrazol-4-yl)-1-isobutyl-3-propyl-1H-pyrrolo[3,2-d]pyrimidine-2,6-dione.

EXAMPLE 34

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 35

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 36

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 37

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 38

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 39

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 40

A subcutaneous formulation may be prepared as follows:

| Ingredient | Quantity |
| --- | --- |
| Active Ingredient | 5.0 mg |
| Corn Oil | 1.0 mL |

EXAMPLE 41

An injectable preparation is prepared having the following composition:

| Ingredient | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

EXAMPLE 42

A topical preparation is prepared having the following composition:

| Ingredient | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 43

Sustained Release Composition

| Ingredient | Weight Range (%) | Preferred Weight Range (%) | Most Preferred Weight (%) |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and then compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film-forming agent will typically be present in an amount ranging from between 2% and 4% of the tablet weight. Suitable film-forming agents are well known to the art and include, but are not limited to, hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably, the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 44

$A_{2B}$ Adenosine Receptor Assays

Methods

Radioligand Binding for $A_{2B}$ Adenosine Receptor.

Human $A_{2B}$ adenosine receptor cDNA was stably transfected into HEK-293 cells (referred to as HEK-$A_{2B}$ cells). Monolayer of HEK-A2B cells were washed with PBS once and harvested in a buffer containing 10 mM HEPES (pH 7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C. Competition assays were started by mixing 10 nM $^3$H-ZM241385 (Tocris Cookson) with various concentrations of test compounds and 50 μg membrane proteins in TE buffer (50 mM Tris and 1 mM EDTA) supplemented with 1 Unit/mL adenosine deaminase. The assays were incubated for 90 minutes, stopped by filtration using Packard Harvester and washed four times with ice-cold TM buffer (10 mM Tris, 1 mM $MgCl_2$, pH 7.4). Non specific binding was determined in the presence of 10 μM ZM241385. The affinities of compounds (i.e. Ki values) were calculated using GraphPad software.

Radioligand Binding for Other Adenosine Receptors.

Human $A_1$, $A_{2A}$, $A_3$ adenosine receptor cDNAs were stably transfected into either CHO or HEK-293 cells (referred to as CHO-$A_1$, HEK-$A_{2A}$, CHO-$A_3$). Membranes were prepared from these cells using the same protocol as described above. Competition assays were started by mixing 0.5 nM $^3$H-CPX (for CHO-$A_1$), 2 nM $^3$H-ZM241385 (HEK-$A_{2A}$) or 0.1 nM $^{125}$I-AB-MECA (CHO-$A_3$) with various concentrations of test compounds and the perspective membranes in TE buffer (50 mM Tris and 1 mM EDTA fo CHO-$A_1$ and HEK-$A_{2A}$) or TEM buffer (50 mM Tris, 1 mM EDTA and 10 mM $MgCl_2$ for CHO-$A_3$) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 1 μM CPX (CHO-$A_1$), 1 μM ZM241385 (HEK-$A_{2A}$) and 1 μM IB-MECA (CHO-$A_3$). The affinities of compounds (i.e. Ki values) were calculated using GraphPad software.

The compounds of Formula I were shown to have affinity for the $A_{2B}$ adenosine receptor in this assay. The $K_i$ values for several of the compounds of the invention are presented in Table 1 below.

TABLE 1

$K_i$ VALUES

| COMPOUND | $K_i$ (nM) |
|---|---|
| 8-(1-benzyl-1H-pyrazol-4-yl)-1,3-dipropyl-1H-pyrrolo[3,2-d]pyrimidine-2,6-dione | 26 |
| 8-(1-benzyl-1H-pyrazol-4-yl)-7-hydroxy-1,3-dipropyl-1H-pyrrolo[3,2-d]pyrimidine-2,6-dione | 120 |
| 8-(1-(3-fluorobenzyl)-1H-pyrazol-4-yl)-1,3-dipropyl-1H-pyrrolo[3,2-d]pyrimidine-2,6-dione | 13 |
| 1,3-dipropyl-8-(pyridin-4-yl)-7-hydroxy-1H-pyrrolo[3,2-d]pyrimidine-2,6-dione | 12 |
| 1,3-dipropyl-8-(pyridin-2-yl)-7-hydroxy-1H-pyrrolo[3,2-d]pyrimidine-2,6-dione | 129 |
| 8-(1-(3-(trifluoromethyl)benzyl)-1H-pyrazol-4-yl)-7-hydroxy-1,3-dipropyl-1H-pyrrolo[3,2-d]pyrimidine-2,6-dione | 9 |
| 1,3-dipropyl-8-(N-hydroxypyridin-4-yl)-1H-pyrrolo[3,2-d]pyrimidine-2,6-dione | 544 | cAMP measurements.

A monolayer of transfected cells were collected in PBS containing 5 mM EDTA. The cells were washed once with DMEM and resuspended in DMEM containing 1 Unit/mL adenosine deaminase at a density of 100,000-500,000 cells/ml. 100 μl of the cell suspension was mixed with 25 μl containing various agonists and/or antagonists and the reaction was kept at 37° C. for 15 minutes. At the end of 15 minutes, 125 µl 0.2N HCl was added to stop the reaction. Cells were centrifuged for 10 minutes at 1000 rpm. 100 µl of the supernatant was removed and acetylated. The concentrations of cAMP in the supernatants were measured using the direct cAMP assay from Assay Design.

$A_{2A}$ and $A_{2B}$ adenosine receptors are coupled to Gs proteins. Given this coupling, agonists for $A_{2A}$ adenosine receptors (such as CGS21680) and for $A_{2B}$ adenosine receptors (such as NECA) increase the cAMP accumulations. Conversely, $A_{2A}$ and $A_{2B}$ adenosine receptor antagonists prevent the increase in cAMP accumulations-induced by the agonists.

$A_1$ and $A_3$ adenosine receptors are coupled to Gi proteins. Consequently, agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

The compounds of the invention were shown to be $A_{2B}$-antagonists by the above tests.

We claim:

1. A compound having the structure of the formula (I):

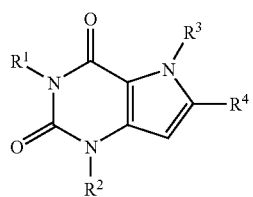

Formula I wherein:
$R^1$ and $R^2$ are independently chosen from hydrogen, optionally substituted alkyl, optionally substituted cycloalkyl, optionally substituted aryl, and optionally substituted heteroaryl;
$R^3$ is chosen from hydrogen, hydroxy, optionally substituted alkyl, optionally substituted cycloalkyl, optionally substituted aryl, and optionally substituted heteroaryl; and
$R^4$ is an optionally substituted heteroaryl moiety, with the proviso that $R^4$ cannot be an unsubstituted five-membered monocyclic heteroaryl ring containing a single S or O hetero atom.

2. The compound of claim 1, wherein
$R^1$ and $R^2$ are independently hydrogen or optionally substituted lower alkyl;
$R^3$ is hydrogen or hydroxyl; and
$R^4$ is an optionally substituted five or six membered monocyclic heteroaryl moiety.

3. The compound of claim 2, wherein $R^4$ is an optionally substituted five membered heteroaryl moiety.

4. The compound of claim 3, wherein $R^4$ contains at least two heteroatoms selected from the group consisting of nitrogen, oxygen, and sulfur.

5. The compound of claim 4, wherein $R^4$ contains at least two nitrogen heteroatoms.

6. The compound of claim 5, wherein $R^4$ is an optionally substituted pyrazole moiety.

7. The compound of claim 6, wherein $R^4$ is substituted with 1 to 3 substituents independently selected from the group consisting of optionally substituted alkyl, optionally substituted heteroaryl, and optionally substituted aryl moieties.

8. The compound of claim 3, wherein $R^4$ is an optionally substituted five membered heteroaryl moiety containing only one heteroatom.

9. The compound of claim 8, wherein $R^4$ contains a single N heteroatom and is optionally substituted with 1 to 3 substituents independently selected from the group consisting of optionally substituted alkyl, optionally substituted heteroaryl, and optionally substituted aryl moieties.

10. The compound of claim 2, wherein $R^4$ is an optionally substituted six membered heteroaryl moiety.

11. The compound of claim 10, wherein $R^4$ is a pyridine moiety optionally substituted with 1 to 3 substituents independently selected from the group consisting of optionally substituted alkyl, optionally substituted heteroaryl, and optionally substituted aryl moieties.

12. The compound of claim 1, wherein the compound is selected from the group consisting of
8-(1-methyl-1H-pyrrol-2-yl)-1,3-dipropyl-1H-pyrrolo[3,2-d]pyrimidine-2,6-dione;
8-(1-(3-(trifluoromethyl)benzyl)-1H-pyrazol-4-yl)-1,3-dipropyl-1H-pyrrolo[3,2-d]pyrimidine-2,6-dione;
8-(1-benzyl-1H-pyrazol-4-yl)-1,3-dipropyl-1H-pyrrolo[3,2-d]pyrimidine-2,6-dione;
8-(1-benzyl-1H-pyrazol-4-yl)-7-hydroxy-1,3-dipropyl-1H-pyrrolo[3,2-d]pyrimidine-2,6-dione;
8-(1-(3-fluorobenzyl)-1H-pyrazol-4-yl)-1,3-dipropyl-1H-pyrrolo[3,2-d]pyrimidine-2,6-dione;
8-(pyridin-4-yl)-1,3-dipropyl-7-hydroxy-1H-pyrrolo[3,2-d]pyrimidine-2,6-dione;
8-(pyridin-2-yl)-1,3-dipropyl-7-hydroxy-1H-pyrrolo[3,2-d]pyrimidine-2,6-dione;
8-(5-(thiophen-2-yl)isoxazol-3-yl)-1,3-dipropyl-1H-pyrrolo[3,2-d]pyrimidine-2,6-dione;
8-(1-(3-(trifluoromethyl)benzyl)-1H-pyrazol-4-yl)-7-hydroxy-1,3-dipropyl-1H-pyrrolo[3,2-d]pyrimidine-2,6-dione; and
8-(N-hydroxypyridin-4-yl)-1,3-dipropyl-1H-pyrrolo[3,2-d]pyrimidine-2,6-dione.

13. A method of treating a pulmonary disorder selected from asthma and pulmonary fibrosis, comprising administering to a mammal in need thereof a therapeutically effective dose of a compound structure of the Formula (I):

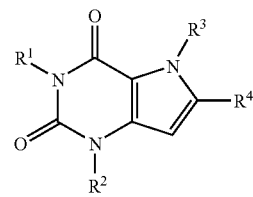

Formula I wherein:
$R^1$ and $R^2$ are independently chosen from hydrogen, optionally substituted alkyl, optionally substituted cycloalkyl, optionally substituted aryl, and optionally substituted heteroaryl;
$R^3$ is chosen from hydrogen, hydroxy, optionally substituted alkyl, optionally substituted cycloalkyl, optionally substituted aryl, and optionally substituted heteroaryl; and
$R^4$ is an optionally substituted heteroaryl moiety, with the proviso that $R^4$ cannot be an unsubstituted five-membered monocyclic heteroaryl ring containing a single S or O hetero atom.

14. The method of claim 13, wherein the pulmonary disorder is asthma.

15. The method of claim 13, wherein the pulmonary disorder is pulmonary fibrosis.

16. A pharmaceutical formulations, comprising a therapeutically effective amount of a therapeutically effective dose of a compound having the structure of the Formula (I):

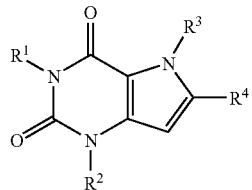

Formula I wherein:
- $R^1$ and $R^2$ are independently chosen from hydrogen, optionally substituted alkyl, optionally substituted cycloalkyl, optionally substituted aryl, and optionally substituted heteroaryl;
- $R^3$ is chosen from hydrogen, hydroxy, optionally substituted alkyl, optionally substituted cycloalkyl, optionally substituted aryl, and optionally substituted heteroaryl; and
- $R^4$ is an optionally substituted heteroaryl moiety, with the proviso that $R^4$ cannot be a five-membered monocyclic heteroaryl ring containing a single S or O hetero atom;

and at least one pharmaceutically acceptable excipient.

* * * * *